US009171711B2

(12) United States Patent
Schneider et al.

(10) Patent No.: US 9,171,711 B2
(45) Date of Patent: *Oct. 27, 2015

(54) METHOD AND SYSTEM FOR VACUUM DRIVEN MASS SPECTROMETER INTERFACE WITH ADJUSTABLE RESOLUTION AND SELECTIVITY

(71) Applicant: DH Technologies Development Pte. Ltd., Singapore (SG)

(72) Inventors: Bradley B. Schneider, Bradford (CA); Thomas R. Covey, Richmond Hill (CA)

(73) Assignee: DH Technologies Development Pte. Ltd. (SG)

( * ) Notice: Subject to any disclaimer, the term of this patent is extended or adjusted under 35 U.S.C. 154(b) by 0 days.

This patent is subject to a terminal disclaimer.

(21) Appl. No.: 13/967,589

(22) Filed: Aug. 15, 2013

(65) Prior Publication Data

US 2014/0117221 A1    May 1, 2014

Related U.S. Application Data

(63) Continuation of application No. 13/541,414, filed on Jul. 3, 2012, now Pat. No. 8,513,600, which is a continuation of application No. 12/783,854, filed on May 20, 2010, now abandoned, which is a continuation-in-part of application No. 12/473,859, filed on May 28, 2009, now Pat. No. 8,084,736.

(60) Provisional application No. 61/057,242, filed on May 30, 2008, provisional application No. 61/178,675, filed on May 15, 2009.

(51) Int. Cl.
*H01J 49/24* (2006.01)
*H01J 49/26* (2006.01)
*G01N 27/62* (2006.01)
*H01J 49/00* (2006.01)
*H01J 49/04* (2006.01)

(52) U.S. Cl.
CPC .............. *H01J 49/26* (2013.01); *G01N 27/622* (2013.01); *H01J 49/004* (2013.01); *H01J 49/0404* (2013.01); *H01J 49/0468* (2013.01); *H01J 49/24* (2013.01)

(58) Field of Classification Search
CPC ......... H01J 49/04; H01J 49/045; H01J 49/02; H01J 49/0422; H01J 49/0468; H01J 49/067; H01J 49/24; H01J 49/26
USPC .................................. 250/281, 282, 288, 289
See application file for complete search history.

(56) References Cited

U.S. PATENT DOCUMENTS 6,504,149 B2 * 1/2003 Guevremont et al. ........ 250/286
6,770,875 B1 * 8/2004 Guevremont et al. ........ 250/288
7,045,778 B2 * 5/2006 Guevremont et al. ........ 250/288

(Continued)

*Primary Examiner* — Nicole Ippolito
*Assistant Examiner* — David E Smith

(57) ABSTRACT

A mass spectrometer system and method of operating same are provided. The system comprises an ion conduit for receiving ions; a boundary member defining a curtain gas chamber containing the ion conduit; a curtain gas supply for providing a curtain gas to an inlet of the ion conduit to provide a gas flow into the conduit, and a curtain gas outflow out of a curtain gas chamber inlet; a mass spectrometer at least partially sealed to, and in fluid communication with, the conduit for receiving the ions from the conduit; a vacuum chamber surrounding the mass spectrometer operable to draw the gas flow including the ions through the conduit and into the vacuum chamber; and, a gas outlet for drawing a gas outflow from the gas flow located between the conduit and the mass spectrometer to increase the gas flow rate through the conduit.

19 Claims, 13 Drawing Sheets

(56) References Cited

U.S. PATENT DOCUMENTS

| | | | |
|---|---|---|---|
| 7,399,958 B2 * | 7/2008 | Miller et al. | 250/286 |
| 8,084,736 B2 * | 12/2011 | Schneider et al. | 250/289 |
| 2005/0035287 A1 * | 2/2005 | Jolliffe et al. | 250/288 |
| 2005/0061964 A1 * | 3/2005 | Nagano et al. | 250/281 |
| 2006/0255261 A1 * | 11/2006 | Whitehouse et al. | 250/288 |
| 2010/0282961 A1 * | 11/2010 | Miller et al. | 250/282 |

* cited by examiner

METHOD AND SYSTEM FOR VACUUM DRIVEN MASS SPECTROMETER INTERFACE WITH ADJUSTABLE RESOLUTION AND SELECTIVITY

This application is a continuation of U.S. application Ser. No. 13/541,414 filed on Jul. 3, 2012, which is a continuation of U.S. application Ser. No. 12/783,854 filed on May 20, 2012 which is a continuation-in-part of U.S. application Ser. No. 12/473,859 filed on May 28, 2009, which in turn claims priority from U.S. Provisional Application No. 61/057,242 filed May 30, 2008 and U.S. Provisional Application No. 61/178,675 filed May 15, 2009. The contents of U.S. application Ser. Nos. 13/541,414, 12/783,854, 12/473,859, 61/057,242 and 61/178,675 are incorporated herein by reference.

INTRODUCTION

The present invention relates generally to methods and systems involving both a mass spectrometer and a differential mobility spectrometer.

In differential mobility spectrometer/mass spectrometer systems, a drift gas is typically supplied from a compressed gas source upstream of the differential mobility spectrometer. This drift gas acts as a carrier gas flow through the differential mobility spectrometer. The delivery of the drift gas to the differential mobility spectrometer can be controlled by flow restriction valves. Sensitivity is related to the transmission efficiency of the system—what percentage of the ions end up being actually detected. Selectivity or resolution refers to the detector's ability to distinguish between similar ions.

Differential mobility spectrometry, also referred to as high field asymmetric waveform ion mobility spectrometry (FAIMS) or Field Ion Spectrometry (FIS), is a variant of ion mobility spectrometry (IMS). IMS separates ions by the difference in the time it takes for them to drift through a gas, typically at atmospheric pressure, in a constant electrostatic field of low field strength applied along the axial length of a flight tube. Ions are pulsed into the flight tube and their flight times are recorded. The time of flight is inversely related to the mobility of an ion. Ions have a single motion of direction (axial) and are separated according to their mobility through the gas under these low field conditions (E<1000V/cm). The drift time and thus mobility is a function of the size and shape of an ion and its interactions with the background gas.

Differential mobility spectrometry differs from IMS in the geometry of the instrumentation and adds an additional dimension to the separation theory. RF voltages, often referred to as separation voltages (SV), are applied across the ion transport chamber, perpendicular to the direction of the transport gas flow. Ions will migrate toward the walls and leave the flight path unless their trajectory is corrected by a counterbalancing voltage, a DC potential often referred to as a compensation voltage (CV). Instead of recording the flight time of an ion through the chamber, the voltage required to correct the trajectory of a particular ion is recorded. Ions are not separated in time as with an IMS: instead, the mobility measurement is a function of the compensation voltage used to correct the tilt in ion trajectory caused by the difference between high field and low field ion mobilities. As such, ions are not pulsed into the analyzer but instead introduced in a continuous fashion and the compensation voltage is scanned to serially pass ions of different differential mobility or set to a fixed value to pass only ion species with a particular differential mobility.

SUMMARY OF THE INVENTION

Typically, there is a tradeoff between selectivity and sensitivity, both of which are linked to the residence time of the ions in the differential mobility spectrometer. Specifically, increasing the residence time of the ions in the differential mobility spectrometer may increase selectivity, but at the price of reducing sensitivity.

As described above, in the description that follows, sensitivity is related to the transmission efficiency of the system—what percentage of the ions end up being actually detected. Selectivity or resolution refers to the detector's ability to distinguish between similar ions.

In accordance with an aspect of an embodiment of the invention, there is provided a mass spectrometer system comprising:
a) an ion conduit for receiving ions from an ion source, the ion conduit having an internal operating pressure;
b) a boundary member defining a curtain gas chamber containing the ion conduit;
c) a curtain gas supply for providing a curtain gas directed by the boundary member to an inlet of the ion conduit to dry and decluster the ions and to provide a gas flow into the ion conduit, and a curtain gas outflow out of a curtain gas chamber inlet;
d) a mass spectrometer at least partially sealed to, and in fluid communication with, the ion conduit for receiving the ions from the ion conduit;
e) a vacuum chamber surrounding the mass spectrometer for maintaining the mass spectrometer at a vacuum pressure lower than the internal operating pressure, such that the vacuum chamber is operable to draw the gas flow including the ions through the ion conduit and into the vacuum chamber; and, f) a gas outlet for drawing a gas outflow from the gas flow located between the ion conduit and the mass spectrometer to increase the gas flow rate through the ion conduit, the gas outlet being located between the ion conduit and the mass spectrometer.

In accordance with an aspect of another embodiment of the invention, there is provided a method of operating a mass spectrometer system including an ion conduit contained in a curtain gas chamber, and a mass spectrometer contained in a vacuum chamber at least partially sealed to, and in fluid communication with, the ion conduit. The method comprises: a) maintaining the ion conduit at an internal operating pressure by directing a curtain gas to an inlet of the ion conduit to dry and decluster the ions and to provide a gas flow into the ion conduit;
b) providing a curtain gas outflow out of a curtain gas chamber inlet of the curtain gas chamber;
c) providing ions to the ion conduit;
d) maintaining the mass spectrometer at a vacuum pressure lower than the internal operating pressure to draw the gas flow including the ions through the ion conduit and into the vacuum chamber; and, e) drawing a bleed gas at a bleed gas flow rate from the gas flow between the ion conduit and the mass spectrometer to increase a gas flow rate through the ion conduit.

BRIEF DESCRIPTION OF THE DRAWINGS

The skilled person in the art will understand that the drawings, described below, are for illustration purposes only. The drawings are not intended to limit the scope of the applicant's teachings in any way.

DESCRIPTION OF VARIOUS EMBODIMENTS

Figure 1:
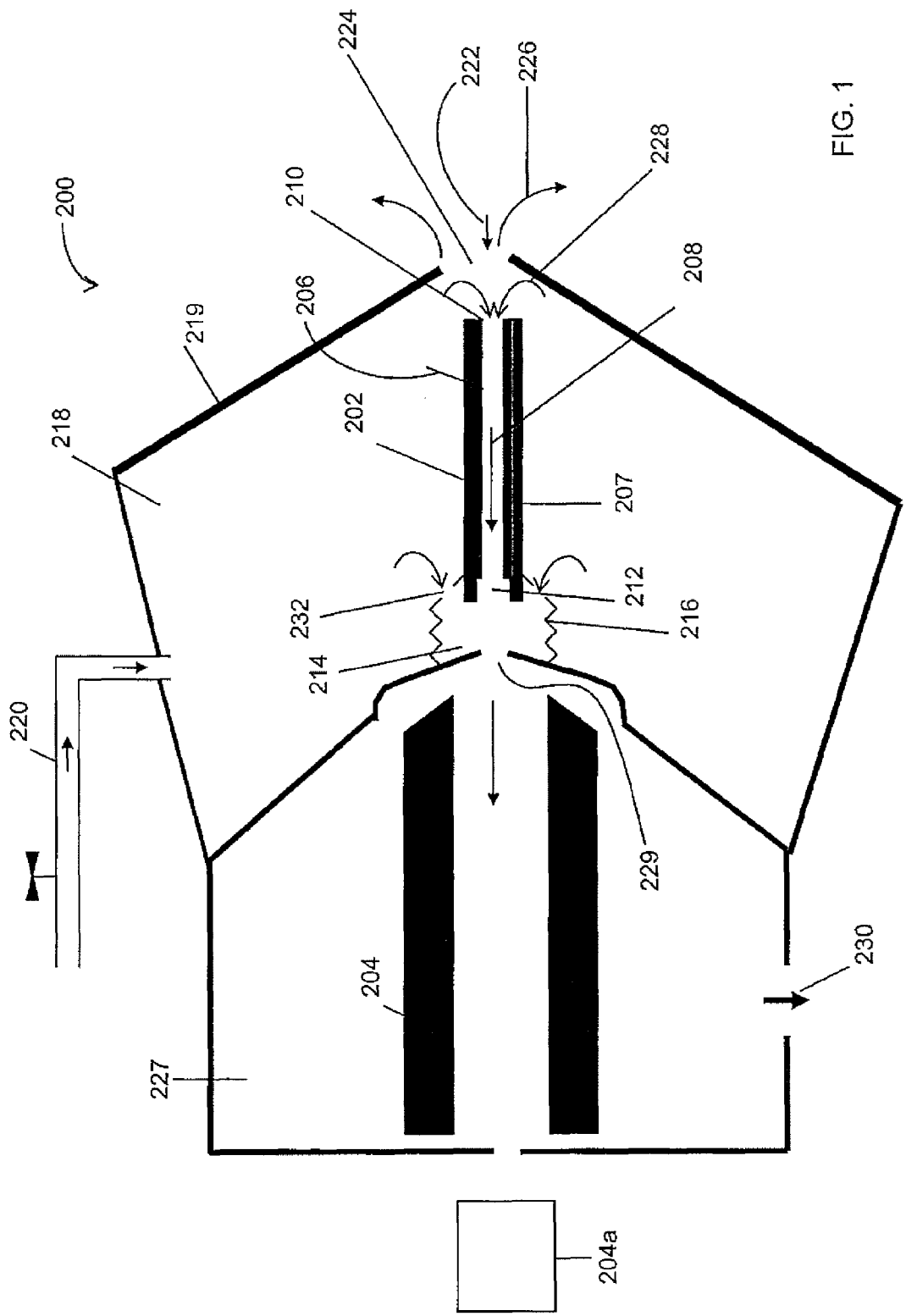
FIG. 1, in a schematic diagram, illustrates a differential mobility spectrometer/mass spectrometer system including a juncture chamber to which a throttle gas is added between the differential mobility spectrometer and the mass spectrometer in accordance with an aspect of a first embodiment of the present invention.

Referring to FIG. 1, there is illustrated in a schematic view, a differential mobility spectrometer/mass spectrometer system 200 in accordance with an aspect of a first embodiment of the present invention. The differential mobility spectrometer/mass spectrometer system 200 comprises a differential mobility spectrometer 202 and a first vacuum lens element 204 of a mass spectrometer (hereinafter generally designated mass spectrometer 204). Mass spectrometer 204 also comprises mass analyzer elements 204a downstream from vacuum chamber 227. Ions can be transported through vacuum chamber 227 and may be transported through one or more additional differentially pumped vacuum stages prior to the mass analyzer indicated schematically as mass analyzer elements 204a. For instance in one embodiment, a triple quadrupole mass spectrometer may comprise three differentially pumped vacuum stages, including a first stage maintained at a pressure of approximately 2.3 Torr, a second stage maintained at a pressure of approximately 6 mTorr, and a third stage maintained at a pressure of approximately $10^{-5}$ Torr. The third vacuum stage may contain a detector, as well as two quadrupole mass analyzers with a collision cell located between them. It will be apparent to those of skill in the art that there may be a number of other ion optical elements in the system that have not been described. This example is not meant to be limiting as it will also be apparent to those of skill in the art that the differential mobility spectrometer/mass spectrometer coupling described can be applicable to many mass spectrometer systems that sample ions from elevated pressure sources. These may include time of flight (TOF), ion trap, quadrupole, or other mass analyzers as known in the art.

The differential mobility spectrometer 202 comprises plates 206 and an electrical insulator 207 along the outside of plates 206. The plates 206 surround a drift gas 208 that drifts from an inlet 210 of the differential mobility spectrometer to an outlet 212 of the differential mobility spectrometer 202. The insulator 207 supports the electrodes and isolates them from other conductive elements. For example, the insulator may be fabricated from ceramic or Teflon™. The outlet 212 of the differential mobility spectrometer 202 releases the drift gas into a juncture or baffle chamber 214 defined by baffles 216, which juncture chamber 214 defines a path of travel for ions between the differential mobility spectrometer 202 and the mass spectrometer 204. In some embodiments, the outlet 212 of the differential mobility spectrometer 202 is aligned with the inlet of the mass spectrometer 204 to define the ion path of travel therebetween, while the baffles 216 are spaced from this path of travel to limit interference of the baffles 216 with the ions 222 traveling along the path of travel.

The differential mobility spectrometer 202 and juncture chamber 214 are both contained within a curtain chamber 218, defined by curtain plate (boundary member) 219 and supplied with a curtain gas from a curtain gas source 220. The curtain gas source 220 provides the curtain gas to the interior of the curtain chamber 218. Ions 222 are provided from an ion source (not shown) and are emitted into the curtain chamber 218 via curtain chamber inlet 224. The pressure of the curtain gas within the curtain chamber 218 provides both a curtain gas outflow 226 out of curtain gas chamber inlet 224, as well as a curtain gas inflow 228 into the differential mobility spectrometer 202, which inflow 228 becomes the drift gas 208 that carries the ions 222 through the differential mobility spectrometer 202 and into the juncture chamber 214. The curtain plate 219 may be connected to a power supply to provide an adjustable DC potential to it.

As illustrated in FIG. 1, the first vacuum lens element 204 of the mass spectrometer 204 is contained within a vacuum chamber 227, which can be maintained at a much lower pressure than the curtain chamber 218. In accordance with an aspect of an embodiment of the present invention, the vacuum chamber 227 can be maintained at a pressure of 2.3 Torr by a vacuum pump 230 while the curtain chamber 218 and an internal operating pressure of the differential mobility spectrometer 202 can be maintained at a pressure of 760 Torr. As a result of the significant pressure differential between the curtain chamber 218 and the vacuum chamber 227, the drift gas 208 is drawn through the differential mobility spectrometer 202, the juncture chamber 214 and, via vacuum chamber inlet 229, into the vacuum chamber 227 and first vacuum lens element 204. As shown, the mass spectrometer 204 can be sealed to (or at least partially sealed), and in fluid communication with the differential mobility spectrometer, via the juncture chamber, to receive the ions 222 from the differential mobility spectrometer 202.

As shown, the baffles 216 of the curtain chamber comprise a controlled leak or gas port 232 for admitting the curtain gas into the juncture chamber 214. Within the juncture chamber 214, the curtain gas becomes a throttle gas that throttles back the flow of the drift gas 208 through the differential mobility spectrometer 202. Specifically, the throttle gas within the juncture chamber 214 modifies a gas flow rate within the differential mobility spectrometer 202 and into the juncture chamber 214, thereby controlling the residence time of the ions 222 within the differential mobility spectrometer 202. By controlling the residence time of the ions 222 within the differential mobility spectrometer 202, resolution and sensitivity can be adjusted. That is, increasing the residence times of the ions 222 within the differential mobility spectrometer 202 can increase the resolution, but can also result in additional losses of the ions, reducing sensitivity. In some embodiments it can therefore be desirable to be able to precisely control the amount of throttle gas that is added to the juncture chamber 214 to provide a degree of control to the gas flow rate through the differential mobility spectrometer 202, thereby controlling the tradeoff between sensitivity and selectivity. In the embodiment of FIG. 1, the inflow of throttle gas from the curtain chamber 218 can be controlled by controlling the size of the leak provided by the gas port 232.

The baffles can be configured to provide a randomizer surface member, and the gas port 232 can be oriented to direct the throttle gas at least somewhat against the baffles 216 and randomizer surface to disburse the throttle gas throughout the juncture chamber 214. In one embodiment, the gas port 232 introduces the throttle gas without disrupting the gas streamlines between the differential mobility spectrometer 202 and the mass spectrometer inlet 229.

As described above and as known in the art, RF voltages, often referred to as separation voltages (SV), can be applied across an ion transport chamber of a differential mobility spectrometer perpendicular to the direction of drift gas 208 (shown in FIG. 1). The RF voltages may be applied to one or both of the DMS electrodes comprising the differential mobility spectrometer. The tendency of ions to migrate toward the walls and leave the path of the DMS can be corrected by a DC potential often referred to as a compensation voltage (CV). The compensation voltage may be generated by applying DC potentials to one or both of the DMS electrodes comprising the differential mobility spectrometer. As is known in the art, a DMS voltage source (not shown) can be provided to provide both the RF SV and the DC CV. Alternatively, multiple voltage sources may be provided.

Similarly, a DC declustering or inlet potential can be provided to the vacuum chamber inlet 229 (again as shown in FIG. 1) by an inlet potential voltage source (not shown), again as known in the art. This vacuum chamber inlet may be a orifice, or, alternatively, may be a capillary, heated, capillary or an ion pipe.

In embodiments of the present invention in which the vacuum chamber inlet 229 is smaller then an outlet of the differential mobility spectrometer 202, it can be advantageous to provide a braking potential to the vacuum chamber inlet 229 relative to the differential mobility spectrometer 202. This braking potential can be provided by providing a DMS DC offset voltage to the plates or electrodes of the DMS relative to the declustering or inlet potential provided to the vacuum chamber inlet 229. By slowing down the ions prior to them entering the vacuum chamber 229, the braking potential can increase the extent to which these ions are entrained within the gas flows, thereby increasing the likelihood that the ions will actually pass through the vacuum chamber inlet, instead of impacting on the sides of the vacuum chamber inlet 229.

Alternatively, in some embodiments of the present invention, such as, for example without limitation, embodiments in which the vacuum chamber inlet 229 is larger relative to the slit or outlet from the differential mobility spectrometer 202, it can be desirable to adjust the DMS DC offset voltage. In particular this DC offset voltage may actually be positive to speed up ions as they pass through the vacuum chamber inlet 229, if it is not desirable to slow them down to improve transmission from the differential mobility spectrometer 202 into the vacuum chamber 227.

This DMS DC offset can also be adjusted based on a mass of the ions being selected in a differential mobility spectrometer 202. This could be part of a two-stage process. Specifically, the declustering voltage provided to the vacuum chamber inlet 229 can first be adjusted based on the mass of the ions being selected in the differential mobility spectrometer 202. Then, relative to this declustering potential provided to the vacuum chamber inlet 229, the DMS DC offset voltage could be adjusted to enhance transmission from the differential mobility spectrometer 202 through the vacuum chamber inlet 229. Alternatively, the DMS offset DC potential may be selected for a given ion. In some embodiments, a voltage source controller can be set to automatically adjust the DMS electrode DC offsets to maintain the same potential difference relative to the orifice potential. Then the declustering potential or inlet potential may be adjusted, That is, in these embodiments the DMS offset voltage is merely the difference between the DC potential applied to the electrodes as an offset and the inlet voltage. Say, for example, that a preferred DMS offset voltage is −3 V. Then, when the inlet voltage is tuned, the control system can, in these embodiments, maintain that −3 V offset regardless of the current inlet voltage. For instance, if the inlet potential is initially 50 V, the DC potential on the DMS electrodes can be automatically maintained at 47 V (CV=0 situation). If the inlet potential is tuned up to 100 V, the DC applied to the DMS electrodes can be automatically changed to 97 V. The CV=0 situation means that an ion high and low field mobility are either the same, or extremely similar. This may occur if the separation voltage is 0 V, or under some conditions with the separation voltage applied.

Figure 2:
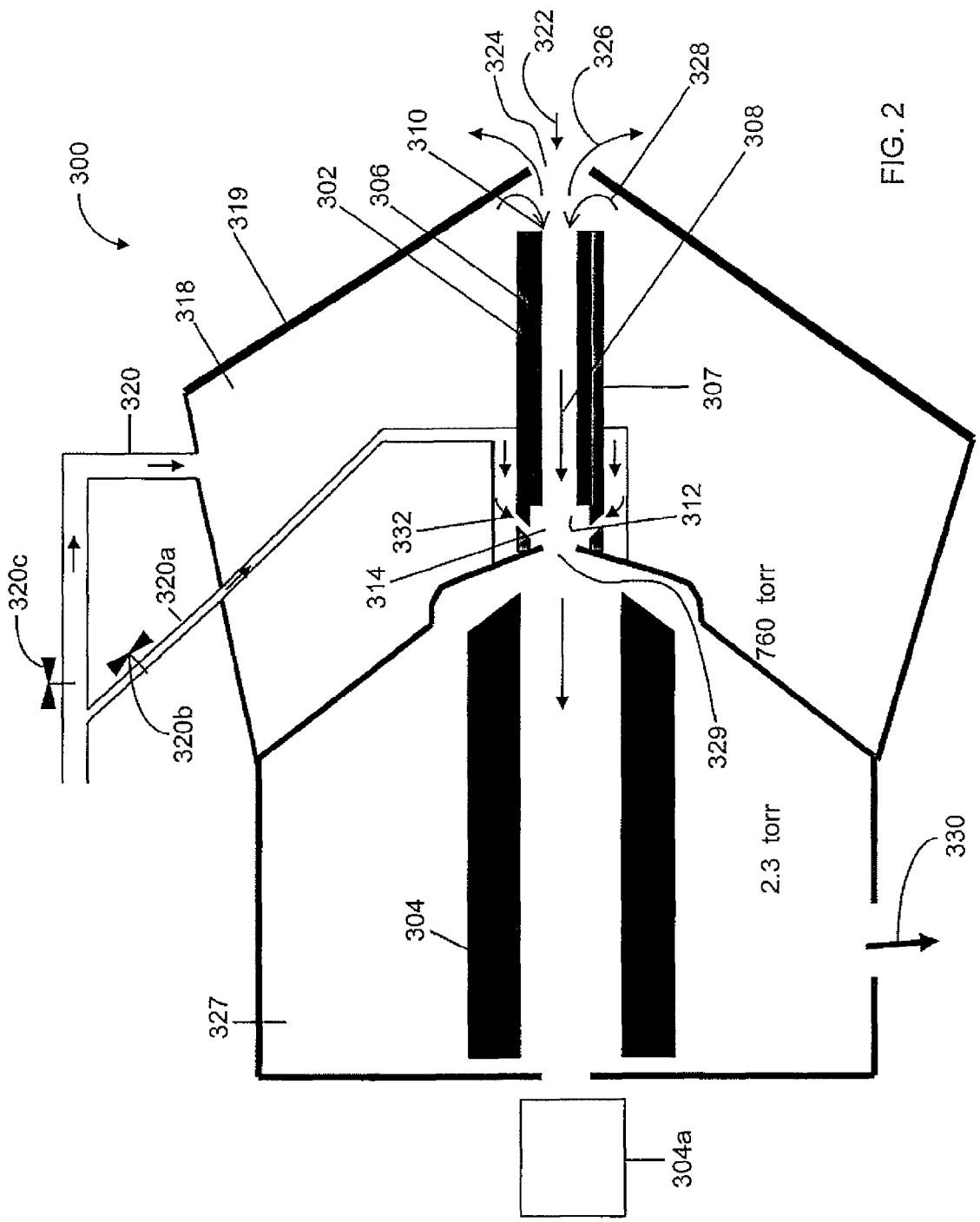
FIG. 2, in a schematic view, illustrates a differential mobility spectrometer/mass spectrometer system including a juncture chamber to which a throttle gas is added between the differential mobility spectrometer and the mass spectrometer in accordance with an aspect of a second embodiment of the present invention.

Referring to FIG. 2, there is illustrated in a schematic view, a differential inability spectrometer/mass spectrometer system 300 in accordance with an aspect of a second embodiment of the present invention. For clarity, the same reference numerals used in FIG. 1, with 100 added, are used in FIG. 2 to designate elements analogous to the elements of FIG. 1. For brevity, the description of FIG. 1 is not repeated with respect to FIG. 2.

It is important to note that due to the compensation voltage provided to the plates or electrodes of the differential mobility spectrometer, the actual DC potential of one or both of the electrodes of the differential mobility spectrometer may not differ by the DMS DC offset amount from the declustering potential applied to vacuum chamber inlet element. For example, say that a declustering potential is applied to vacuum chamber inlet element 329. This declustering potential (DP) is determined based on the m/z of the ion being selected by the differential mobility spectrometer, and this determination of the DP is known in the art. Then, a DC offset voltage is applied to the plate or electrodes 306 of the differential mobility spectrometer 302. In addition, the CV will be applied to the electrodes 306. Application of a CV may proceed in different ways. For example, say that there is a CV of 10 volts, then 5V can be applied to one electrode, while −5V are applied to the other electrode. Alternatively, 10V can be applied to one electrode and no volts to the other electrode.

Consider an example where all of the CV is applied to one electrode. Then, say that a DP of 100V is first determined for the vacuum chamber inlet. The offset between the vacuum chamber inlet and the differential mobility spectrometer is determined to be −5V. The CV for the differential mobility spectrometer is 10V. Then, one electrode of the differential mobility spectrometer would have a potential of 100V −5V+ 10V or 105V, while the other electrode would have a potential of 100V−5V=95V.

As noted above, the DC offset voltage need not be negative. Specifically, where the orifice or inlet dimension more closely matches the slit dimension for the differential mobility spectrometer, there may be no need to slow the ions down to properly entrain them in the gas flow so that they can flow through the orifice. Instead, it could even be desirable to speed the ions up.

Figure 2A:
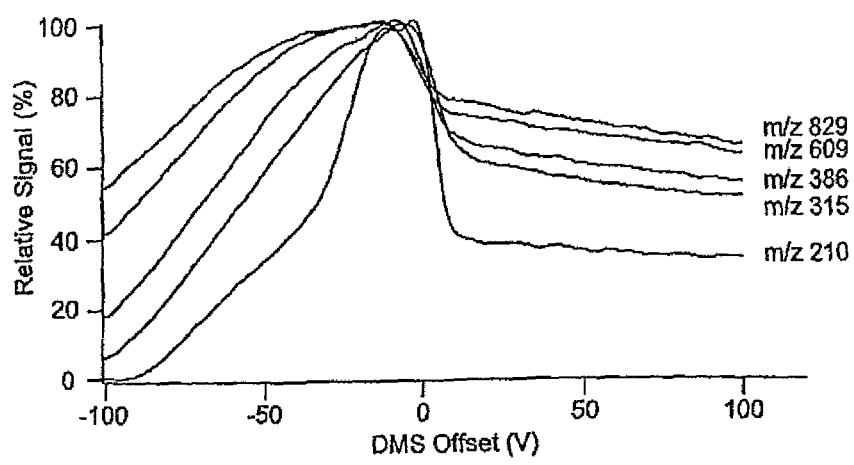
FIG. 2A, in a graph, plots the signals for various ions against the DMS offset potential relative to a potential at the vacuum chamber inlet or mass spectrometer inlet.

Referring to FIG. 2A, the effectiveness of braking potentials applied to electrodes of dimension 1×10×30 mm is plotted in a graph for various mass to charge ratios. For all the ions tested, the optimal DMS offset voltage appears to be negative—that is, the optimal DMS potential should be slightly lower than the vacuum chamber inlet potential to establish a braking potential. The magnitude of the optimal offset voltage and the widths of the optimal voltage range both increase with the mass to charge ratio of the ion of interest, likely reflecting the known decrease in the ion mobility constant for higher m/z ions. The data plotted in FIG. 2A demonstrates that the transfer of ions from a slotted DMS analyzer to a circular mass spectrometer or vacuum chamber inlet may be improved by slowing down the ions to give them a longer time period in which to be influenced by the bending gas streams converging on the inlet, thereby reducing losses in the interface region or juncture of the differential mobility spectrometer and mass spectrometer.

As with the system 200 of FIG. 1, in the system 300 of FIG. 2 drift gas 308 can be drawn through the differential mobility spectrometer 302 and into the vacuum chamber 327 and the first vacuum lens element 304 by the much lower pressure maintained in the vacuum chamber 327. As with the system 200 of FIG. 1, the vacuum chamber 327 of the system 300 can be maintained, say, at a pressure of 2.3 Torr, for example, while the pressure in the curtain chamber 318 can be maintained at a pressure of 760 Torr.

As with the system 200 of FIG. 1, the resolution or selectivity of system 300 can be adjusted by adding a throttle gas to a juncture chamber 314 between the differential mobility spectrometer 302 and the vacuum chamber inlet 329. In the system 300 of FIG. 2, a common source is provided for both the curtain gas and the throttle gas; however, separate sources may also be provided. For example, this gas could be nitrogen. The throttle gas flows through a conduit branch 320a into the juncture chamber 314. Again, this gas is called a throttle gas because it throttles back the flow through the differential mobility spectrometer. In some embodiments, the gas can be added in a coaxial manner to reduce the likelihood of a cross beam of the throttle gas interfering with the ion beam trajectory or ion path of travel between the differential mobility spectrometer 302 and the mass spectrometer, as interference with this ion beam trajectory could potentially diminish transmission efficiency. For example, as shown in FIG. 2, gas ports 332 are oriented or inclined such that the throttle gas flows into the juncture chamber 314 at an orientation that is toward the vacuum chamber 327 and away from the differential mobility spectrometer 302. Optionally, the juncture chamber 314 can be enlarged or may include extra structures to reduce the linear velocity of the throttle gas to reduce its interference with the ion beam at the point of entry into the mass spectrometer. Further, the gas ports 332 may optionally be oriented such that the throttle gas flows along the sidewalls of the juncture chamber, somewhat parallel to the ion path of travel. In another embodiment, the juncture chamber may be designed with a much larger diameter than the diameter of the insulator, and the gas port may be oriented such that the gas stream through the inlet is directed along the wall.

Please note that schematic FIGS. 1-9 are not to scale. That is, from a functional perspective the juncture chamber can be made substantially larger than what is shown in the figures, to reduce the risk of the throttle gas inflow disrupting ion flow through the juncture chamber. Further, the throttle gas can be introduced so as to be directed along the wall, thereby reducing disruption, and increasing sensitivity, as compared to the case in which the throttle gas is provided in a cross-flow to the ion motion in the juncture chamber.

Conduit branch 320a comprises a controllable valve 320b that can be used to control the rate of flow of the throttle gas into the juncture chamber 314. For example, to increase resolution or selectivity, at the price of an acceptable loss in sensitivity, the controllable valve 320b could be opened to admit more throttle gas into the juncture chamber 314 via conduit branch 320a to reduce the gas flow rate within the differential mobility spectrometer 302. This, in turn, can increase the residence time of the ions 322 within the differential mobility spectrometer. The increased residence time manifests itself as narrower mobility peak widths, and therefore, improved selectivity. At the same time, the increased residence time lowers sensitivity somewhat due to increased diffusion losses. At the same time, because of the increased residence time within the differential mobility spectrometer, more of the ions can be lost.

As shown, FIG. 2 also can comprise a valve 320c for controlling the rate of flow of the curtain gas into the curtain chamber 318. It is important to control the curtain gas flow rate to ensure proper declustering of ions upstream of to the DMS. Clusters can have different mobilities than dry ions, and can therefore have different compensation voltage (CV) values. These clusters can be filtered and lost while transmitting an ion of interest, leading to reduced sensitivity. As shown in FIG. 2, the system may comprise a common gas supply to provide both the curtain gas and the throttle gas flows. The curtain gas outflow 326 from the curtain plate 319 aperture can be defined by the sum of the volumetric flow rates for the curtain gas and the throttle gas minus the volumetric flow rate through the gas conductance limiting aperture 329. The curtain gas outflow 326 is typically optimized for a given compound and set of conditions. Therefore, with the configuration illustrated in FIG. 2, the curtain gas outflow 326 may be maintained constant regardless of what portion of the total flow is provided through passage 320 (curtain gas) or 320a (throttle gas), provided that the total volumetric flow rate is constant.

As the differential mobility spectrometer 302 is sealed, or at least partially sealed (no seal is perfect) to the mass spectrometer, or at least to the first vacuum chamber 327, The mass spectrometer can comprise a circular orifice to receive the ions 322 from the differential mobility spectrometer 302. This is enabled by the streamlines resulting from sealing the differential mobility spectrometer 302 to the mass spectrometer. The gas streamlines exiting the differential mobility spectrometer 302 converge on the orifice inlet 329, and these bending streamlines can transportions through the inlet 329. It can be desirable to maintain a circular orifice to ensure high transmission efficiency through subsequent vacuum stages and lenses.

Figure 3:
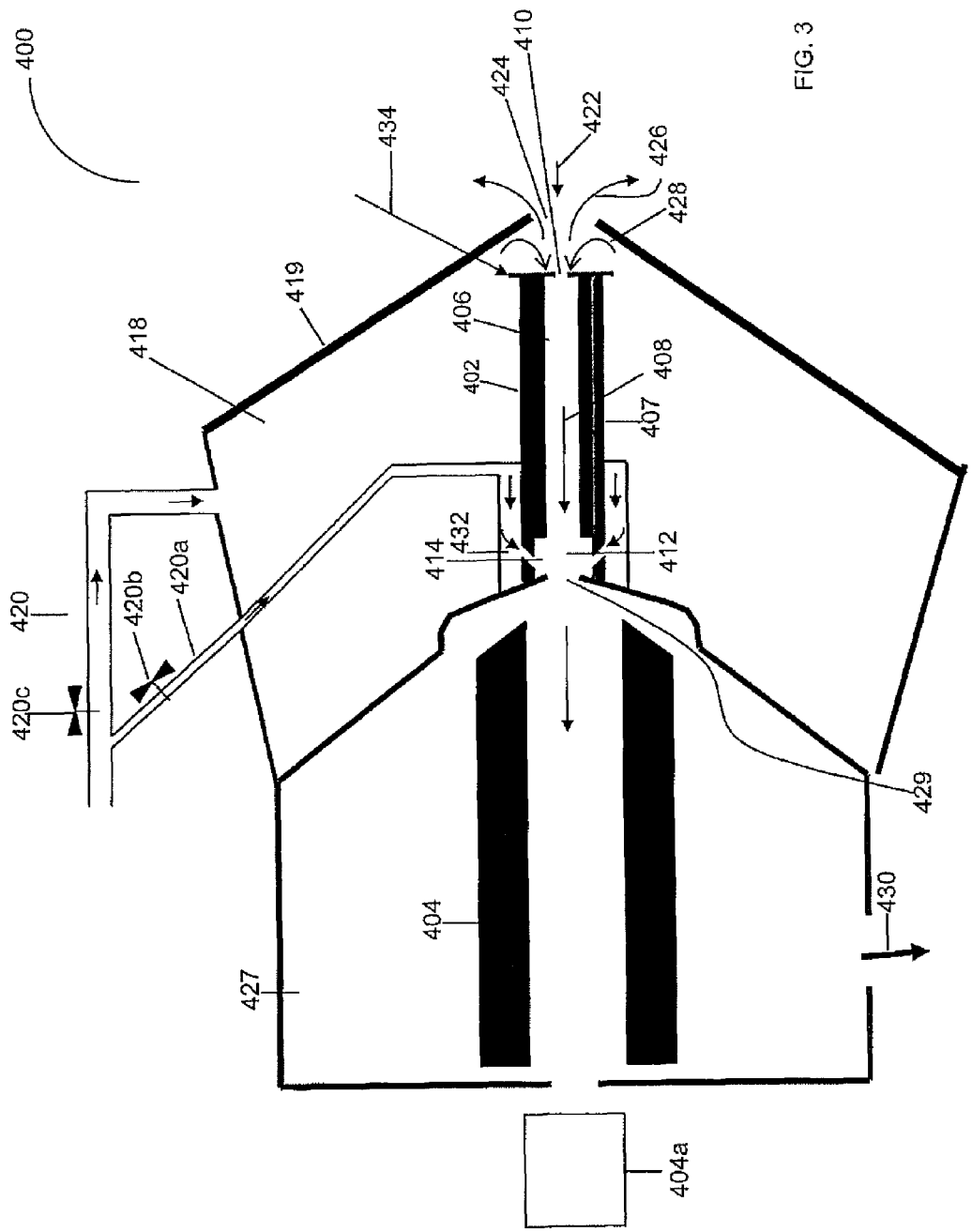
FIG. 3, in a schematic view, illustrates a differential mobility spectrometer/mass spectrometer system including a juncture chamber to which a throttle gas is added between the differential mobility spectrometer and the mass spectrometer, and in which gas flow into the differential mobility spectrometer is restricted, in accordance with an aspect of a third embodiment of the present invention.

Referring to FIG. 3, there is illustrated in a schematic view, a differential mobility spectrometer/mass spectrometer system 400 in accordance with an aspect of a third embodiment of the present invention. For clarity, the same reference numerals used in FIG. 2, with 100 added, are used in FIG. 3 to designate elements analogous to the elements of FIG. 2. For brevity, the descriptions of FIGS. 1 and 2 are not repeated with respect to FIG. 3.

As with the system 300 of FIG. 2, the resolution or selectivity of system 400 of FIG. 3 can be adjusted by adding throttle gas to a juncture chamber 414 between the differential mobility spectrometer 402 and the vacuum chamber inlet 429. As with system 300 of FIG. 2, a common source can be provided for both the curtain gas and the throttle gas.

In addition, gas restriction plates 434 are provided at an inlet 410 of the differential mobility spectrometer 402. These gas restriction plates 434 can facilitate tuning the pressure of the differential mobility spectrometer 402 for further optimization of selectivity, in an analogous fashion to Nazarov et al. (Nazarov E G, Coy S L, Krylov E V, Miller A R, Eiceman G., Pressure Effects in Differential Mobility Spectrometry, *Anal. Chem.*, 2006, 78, 7697-7706). Specifically, when the gas restriction plates 434 are provided to restrict the flow of drift gas into the differential mobility spectrometer 402, pumping at the back of the differential mobility spectrometer 402, by providing the lower pressure in the vacuum chamber 427, can lower the pressure within the differential mobility spectrometer to provide an extra degree of selectivity or an extra parameter to adjust for tricky separations. The diameter of the aperture in the gas restriction plate 434 can be adjustable to allow an operator to tune the pressure within the differential mobility spectrometer 402 for the vacuum draw established with a fixed mass spectrometer inlet diameter.

Figure 4:
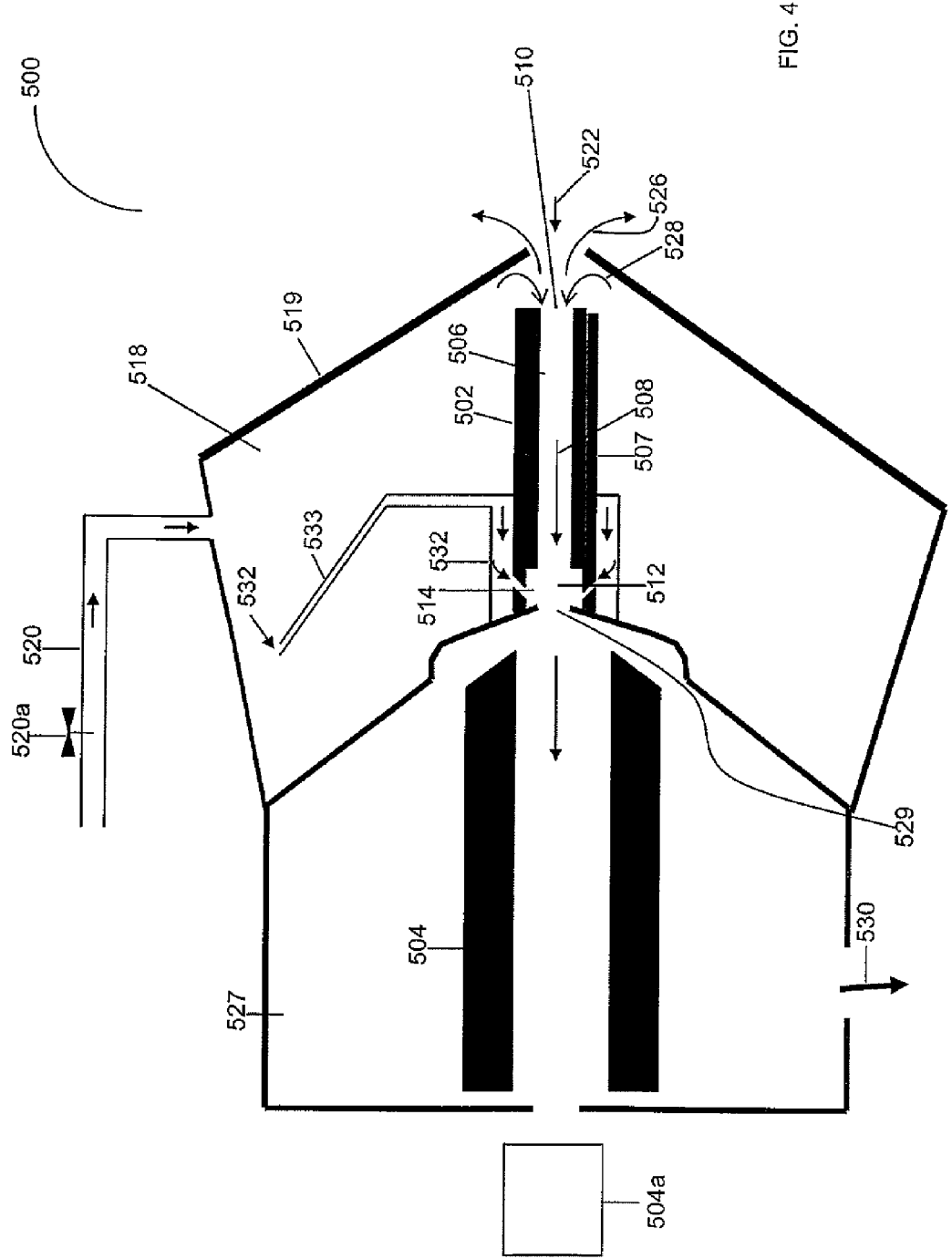
FIG. 4, in a schematic view, illustrates a differential mobility spectrometer/mass spectrometer system in which a controlled leak is provided at a juncture of the differential mobility spectrometer and the mass spectrometer to adjust the gas flow rate through the differential mobility spectrometer in accordance with an aspect of a fourth embodiment of the present invention.

Referring to FIG. 4, there is illustrated in a schematic view a differential mobility spectrometer/mass spectrometer system 500 in accordance with an aspect of a fourth embodiment of the present invention. For clarity, the same reference numerals used in FIG. 1, with 300 added, are used in FIG. 4 to designate elements analogous to the elements of FIG. 1. For brevity, the descriptions of FIG. 1 to 3 are not repeated with respect to FIG. 4.

The system 500 of FIG. 4 is a hybrid of the systems 200 and 300 of FIGS. 1 and 2 respectively. That is, similar to the system 200 in FIG. 1, the curtain gas supply 520 provides a curtain gas to the curtain chamber 518, and a controlled leak 532 is provided from the curtain chamber 518 into the juncture chamber 514. However, similar to the system 300 of FIG. 2, the flow of throttle gas into the juncture chamber 514 of the system 500 of FIG. 4 can be controlled independently of the pressure of the curtain gas within the curtain chamber 518 by adjusting gas flow restrictors 533. That is, gas flow restrictors 533 can be adjusted to adjust the size of controlled leak 532, thereby adjusting the amount of throttle gas sucked into the juncture chamber 514, without mechanically breaking the seal with the mass spectrometer 504. In contrast, the controlled leak 232 of the system 200 of FIG. 1 is provided by mechanically altering the leak provided by the seal with the mass spectrometer as shown in FIG. 1. Specifically, baffles 216 of the system 200 of FIG. 1 are adjustable to control the size of the leak shown in FIG. 1.

Figure 5:
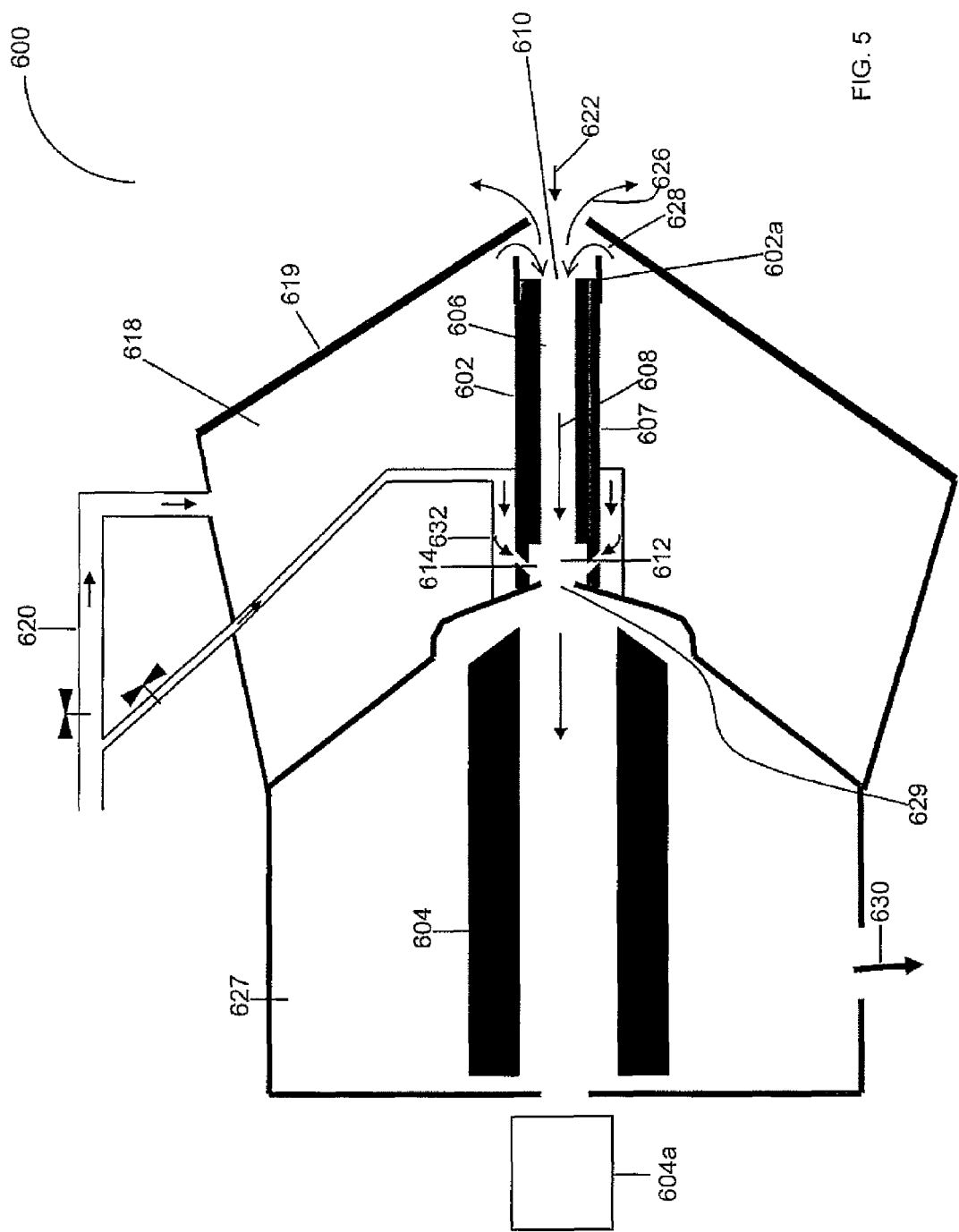
FIG. 5, in a schematic view, illustrates a differential mobility spectrometer/mass spectrometer system including a juncture chamber to which the throttle gas is added between the differential mobility spectrometer and the mass spectrometer and in which the differential mobility spectrometer includes a heated tube in accordance with an aspect of a fifth embodiment of the present invention.

Referring to FIG. 5, there is illustrated in a schematic view, a differential mobility spectrometer/mass spectrometer system 600 in accordance with an aspect of a fifth embodiment of the invention. For clarity the same reference numerals used in FIG. 2, with 300 added are used in FIG. 5 to designate elements analogous to the elements of FIG. 2. For brevity, the descriptions of FIGS. 1 and 2 are not repeated with respect to FIG. 5.

In a system 600 of FIG. 5, a heated tube 602a is installed at the inlet 610 of the differential mobility spectrometer 602. The heated tube 602a can be sealed to the inlet 610 of the differential mobility spectrometer 602. The heated tube 602a can facilitate additional declustering of the ions 622 prior to the ions 622 entering the differential mobility spectrometer. During use with high flow rate high performance liquid chromatography (HPLC), for example clusterring can be a problem that decreases sensitivity. This additional declustering can also help with other ion sources, such as atmospheric pressure matrix-assisted laser desorption/ionization (AP-MALDI), atmospheric pressure chemical ionization (APCI), Desorption electrospray ionization (DESI), and Direct Analysis in Real Time (DART), for example. While these sources have been provided as examples, it will be apparent to those of skill in the art that this approach can improve performance for any ionization source that generates ions as well as clusters. The heated tube 602a can also facilitate laminar flow conditions, and increase the uniformity of the electric field at the inlet 610 of the differential mobility spectrometer 602, and by doing so can facilitate ion transmission into the differential mobility spectrometer 602.

In some embodiments of the present invention, such as the system 600 illustrated in FIG. 5, increases in the volumetric flow of throttle gas into the juncture chamber 614 can be balanced by corresponding reductions in the volumetric flow rate of curtain gas into the curtain chamber 618. For example, the total rate of flow of say, nitrogen, into both the curtain chamber and the juncture chamber (the curtain gas flow rate and the throttle gas flow rate respectively) can be kept substantially constant by balancing changes in one of the curtain gas flow rate and the throttle gas flow rate with opposite changes in the other of these flow rates. This can be desirable.

Specifically, if the flow of throttle gas into the juncture chamber is increased while the flow of curtain gas into the curtain chamber is kept constant, then the outflow of curtain gas away from the inlet of the differential mass spectrometer can be expected to increase. This can be undesirable. That is, as shown in FIG. 5 for example, a particular outflow 626 of curtain gas, in the opposite direction to the flow of gas through the differential mobility spectrometer and into the mass spectrometer, may have been selected for a particular group of ions sharing a common m/z to decluster these ions. Thus, the curtain gas outflow rate desired may depend on the group of ions of interest and what counterflow is desired to help to decluster them. If the flow of throttle gas into the juncture chamber 614 is increased, then, other things equal, the outflow 626 from the boundary member 619 can also be expected to increase beyond what was selected, which can be undesirable. Accordingly, in some embodiments it can be desirable to reduce the inflow of the curtain gas into the curtain chamber proportionally to balance an increase in the inflow of throttle gas into the juncture chamber.

FIG. 5 illustrates one way in which this can be achieved. Specifically, for system 600 a common source is shown for both the curtain gas and the throttle gas. Thus, for example, if a greater flow from this common source is used to increase the rate at which throttle gas flows into the juncture chamber, then there may be a corresponding reduction in the flow rate of the curtain gas from this common source into the curtain chamber. This reduction of the flow rate of curtain gas into the curtain chamber can help to balance the increase in the rate of flow of throttle gas into the juncture chamber, such that the outflow 626 of curtain gas away from the inlet of differential mass spectrometer 602 is substantially unchanged.

This balancing of increases in throttle gas flow with proportional decreases in curtain gas flow can also be achieved using other means in connection with other embodiments of the present invention. For example, in the case of the system 500 of FIG. 4, increasing the curtain gas flow rate into the curtain chamber 518 could, on its own, also increase the rate at which throttle gas flows into the juncture chamber 514, resulting in a significant increase in the outflow 526 from the boundary member 519 relative to the outflow initially selected. However, this effect can be overcome, and the rate at which throttle gas flows into the juncture chamber even reduced, by adjusting gas flow restrictors 533 to reduce the flow of throttle gas into the juncture chamber 514 via controlled leak 532. Of course, where the throttle gas flow rate decreases, the curtain gas flow into the curtain chamber can be proportionally increased, to maintain the outflow of curtain gas away from the inlet of the differential mass spectrometer substantially constant.

Figure 6:
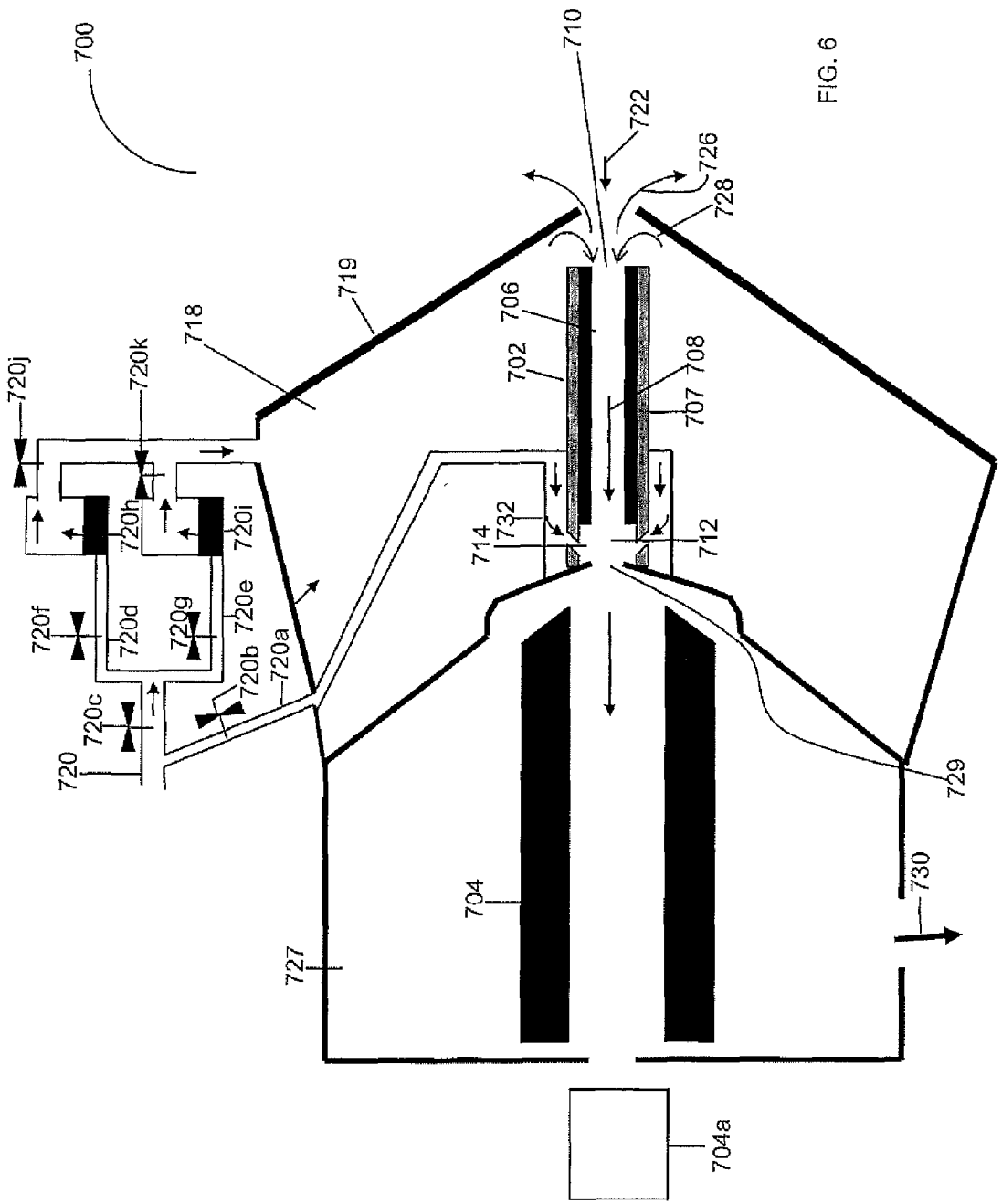
FIG. 6, in a schematic view, illustrates a differential mobility spectrometer/mass spectrometer system similar to that described in FIG. 2, and in which bubblers are provided for adding liquid modifiers to the curtain gas provided to the curtain chamber, in accordance with an aspect of a sixth embodiment of the present invention.

Referring to FIG. 6, there is illustrated in a schematic view a differential mobility spectrometer/mass spectrometer system 700 in accordance with an aspect of a sixth embodiment of the present invention. For clarity, the same reference numerals used in FIG. 2, with 400 added, are used in FIG. 6 to designate elements analogous to the elements of FIG. 2. For brevity the descriptions of preceding Figures, including FIGS. 1 and 2, are not repeated with respect to FIG. 6.

As shown in FIG. 6, the system 700 is quite similar to the system 300 of FIG. 2. However, the system 700 of FIG. 6 comprises additional elements. Specifically, as with the system 300 of FIG. 2, a curtain gas supply 720 comprises a controllable valve 720*b* that can be used to control the rate of flow of the throttle gas into the juncture chamber 714 via conduit branch 720*a*. Conduit or curtain gas supply 720 also comprises a valve 720*c* for controlling the rate of flow of the curtain gas that will ultimately end up in the curtain chamber 718. The flow of the curtain gas downstream of valve 720*c* is divided into two branches 720*d* and 720*e*. The flow of the curtain gas within branch 720*d* is controlled by valve 720*f*. Similarly, the flow of the curtain gas within branch 720*e* is controlled by valve 720*g*.

The flow of the curtain gas through branch 720*d* passes into a bubbler 720*h*, which can be used to add a modifier liquid to the curtain gas/drift gas, which passes through branch 720*d* and will ultimately be pumped into the differential mobility spectrometer 702 by the vacuum maintained in the vacuum chamber 727. Similarly, a separate modifier can be added to the curtain gas flowing through branch 720*e* in bubbler 720*i*. The curtain gas outflows from the bubblers 720*h* and 720*i* can be controlled by outlet valves 720*j* and 720*k* respectively, after which the two branches 720*d* and 720*e* merge and then release the curtain gas with the modifiers into the curtain chamber 718. As noted above, the curtain gas and drift gas are one and the same; thus, adding the modifiers to the curtain gas adds simplicity to the system 700. Modifiers can be vapors that provide selectivity by clustering with ions to different degrees, thereby shifting the differential mobility. Examples of modifiers can include alcohols such as isopropyl alcohol, water, as well as hydrogen and deuterium exchange agents, such as deuterated water or methanol, which can be used, amongst other things, to count the number of exchangeable protons on a molecule. In general, a modifier may be defined as any additive to the drift gas that changes the observed compensation voltage for a peak at a given AC amplitude. The compensation voltage is related to the ratio of high to low field mobility. Modifiers can act in other ways as well as clustering phenomena. For instance, changing the polarizability of the drift gas can also change the observed compensation voltage. Clustering and polarizability changes are two examples of mechanisms that modifiers may use to change compensation voltage optima; however, there may also be many other mechanisms.

Figure 7:
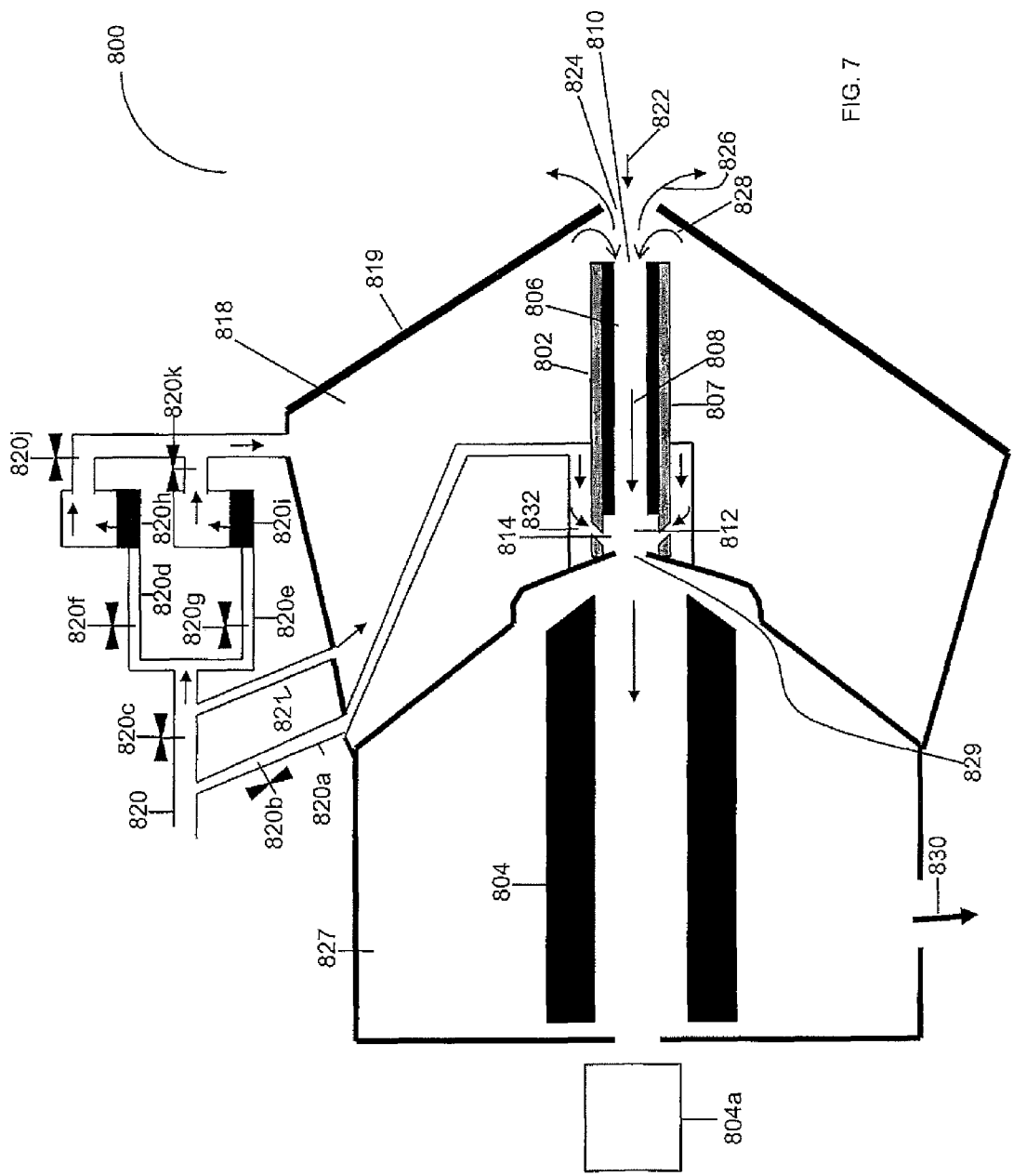
FIG. 7, in a schematic view, illustrates a differential mobility spectrometer/mass spectrometer system similar to that of FIG. 6, but also including an additional conduit branch for providing curtain gas directly to the curtain chamber without any liquid modifiers, in accordance with an aspect of a seventh embodiment of the present invention.

Referring to FIG. 7, there is illustrated in a schematic view a differential mobility spectrometer/mass spectrometer system 800 in accordance with an aspect of a seventh embodiment of the present invention. For clarity, the same reference numerals used in FIG. 6 with 100 added are used in FIG. 7 to designate elements analogous to the elements of FIG. 6. For brevity the descriptions of preceding figures, including FIGS. 1, 2 and 6, are not repeated with respect to FIG. 7.

As shown in FIG. 7, the system 800 is very similar to the system 700 of FIG. 6. However the system 800 of FIG. 7 comprises an additional conduit branch 821. Conduit branch 821 can provide curtain gas, nitrogen in the present case, directly to the curtain chamber 818 without passing through bubblers 820*h* and 820*i* for modifier liquids to be added. Alternatively conduit branch 821 can provide curtain gas directly to chamber 818, while an additional gas fraction can also be added containing one or more modifiers.

Figure 8:
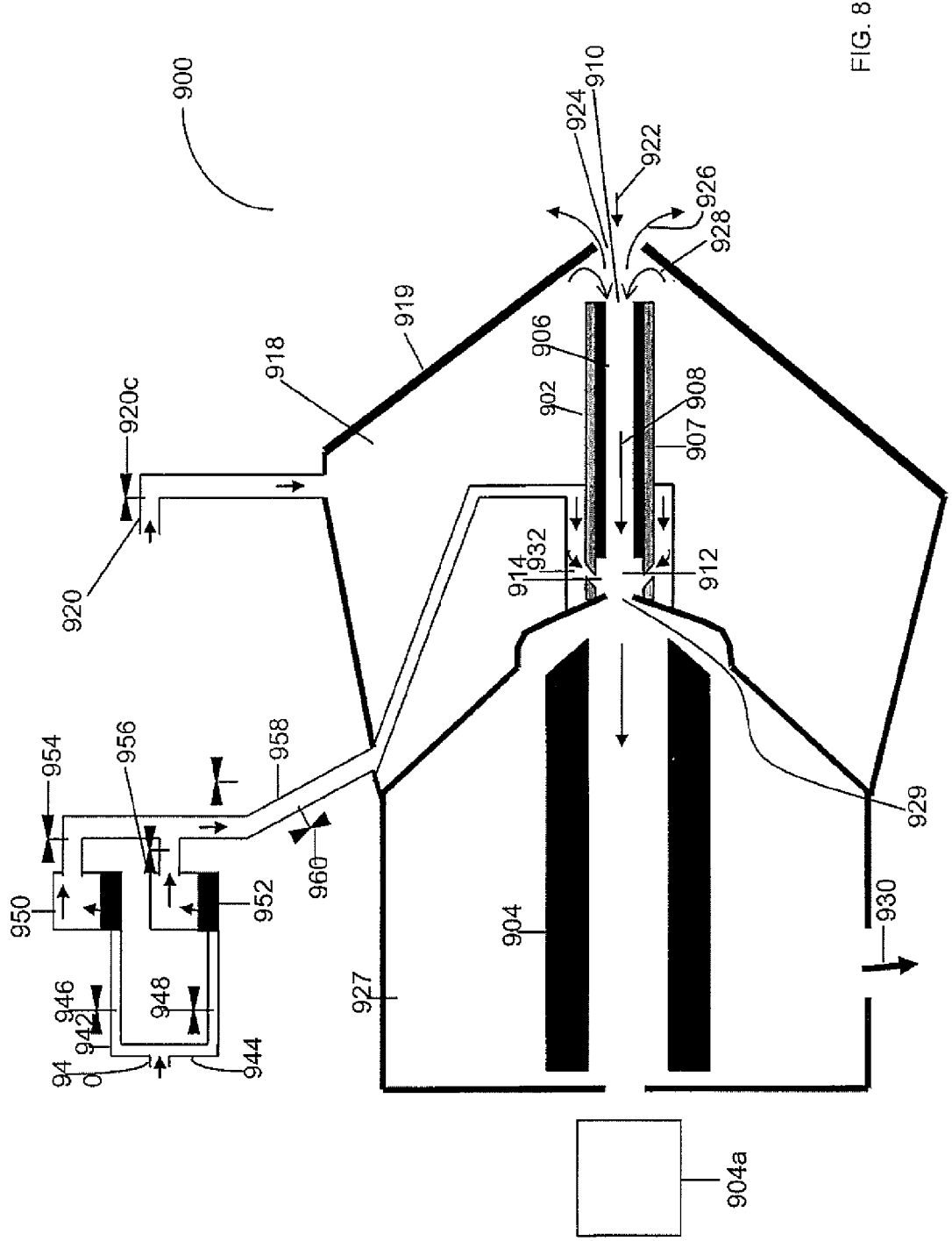
FIG. 8, in a schematic view, illustrates a differential mobility spectrometer/mass spectrometer system including a juncture chamber to which a throttle gas is added between the differential mobility spectrometer and the mass spectrometer, and in which bubblers are provided to add various modifiers to the throttle gas, in accordance with an aspect of a eighth embodiment of the present invention.

Referring to FIG. 8, there is illustrated in a schematic view a differential mobility spectrometer/mass spectrometer system 900 in accordance with an aspect of an eighth embodiment of the present invention. For clarity, the same reference numerals used in FIG. 2, with 600 added, are used in FIG. 8 to designate elements analogous to the elements of FIG. 2. For brevity, the descriptions of preceding figures, including FIGS. 1 and 2 are not repeated with respect to FIG. 8.

As shown in FIG. 8, the system 900 is quite similar to the system 300 in FIG. 2. However, the system 900 in FIG. 8 comprises additional elements. Specifically, as with the system 300 of FIG. 2, a curtain gas supply 920 comprises a controllable valve 920*c* for controlling the rate of flow of the curtain gas into curtain chamber 918. However, unlike the embodiments of FIGS. 2 and 7, separate sources are provided for the curtain gas and the throttle gas. Specifically, the system 900 further comprises a throttle gas source 940 that divides into two branches 942 and 944. The flow of the throttle gas within conduit branch 942 is controlled by controllable valve 946. Similarly, the flow of the throttle gas within branch 944 is controlled by valve 948. Optionally, as described below, auxiliary supplies for supplying auxiliary substances to the juncture chamber via the gas port 932 can be provided.

The flow of throttle gas through branch 942 passes into a bubbler 950, which can be used to add a modifier liquid to the throttle gas passing through branch 942. Similarly, a separate liquid modifier can be added to the throttle gas flowing through branch 944 by bubbler 952. The throttle gas/liquid modifier outflows from the bubblers 950 and 952 can be controlled by outlet valves 954 and 956 respectively, after which the two branches 942 and 944 merge into common branch 958. The flow of the throttle gas and modifier liquids added by bubblers 950 and 952 through conduit 958 and eventually into juncture chamber 914 can be controlled by controllable valve 960.

The various controllable valves 946, 948, 954 and 956 enable liquid modifiers to be added to the throttle gas by bubblers 950 and 952 in a controlled manner to facilitate selectivity by clustering and reacting ions to different degrees thereby shifting their masses observed in the mass spectrometer 904. As described above, the modifiers added may also include hydrogen and deuterium exchange agents, such as deuterated water or methanol, used, amongst other things, to count the number of exchangeable protons on the ions prefiltered with the differential mobility spectrometer.

In the differential mobility spectrometer/mass spectrometer systems of FIGS. 1 to 8, the differential mobility spectrometers can be dimensioned to provide, initially, a relatively short residence time for the ions within the differential mobility spectrometer, and a relatively high gas flow rate of the drift gas within the differential mobility spectrometer. This initial bias of the differential mobility spectrometer in favor of sensitivity at the expense of selectivity can be subsequently offset by providing a throttle gas to the juncture chambers as described above to decrease the flow rate of the drift gas. In the aspects of the embodiments illustrated in FIG. 9, the opposite approach is taken.

Figure 9:
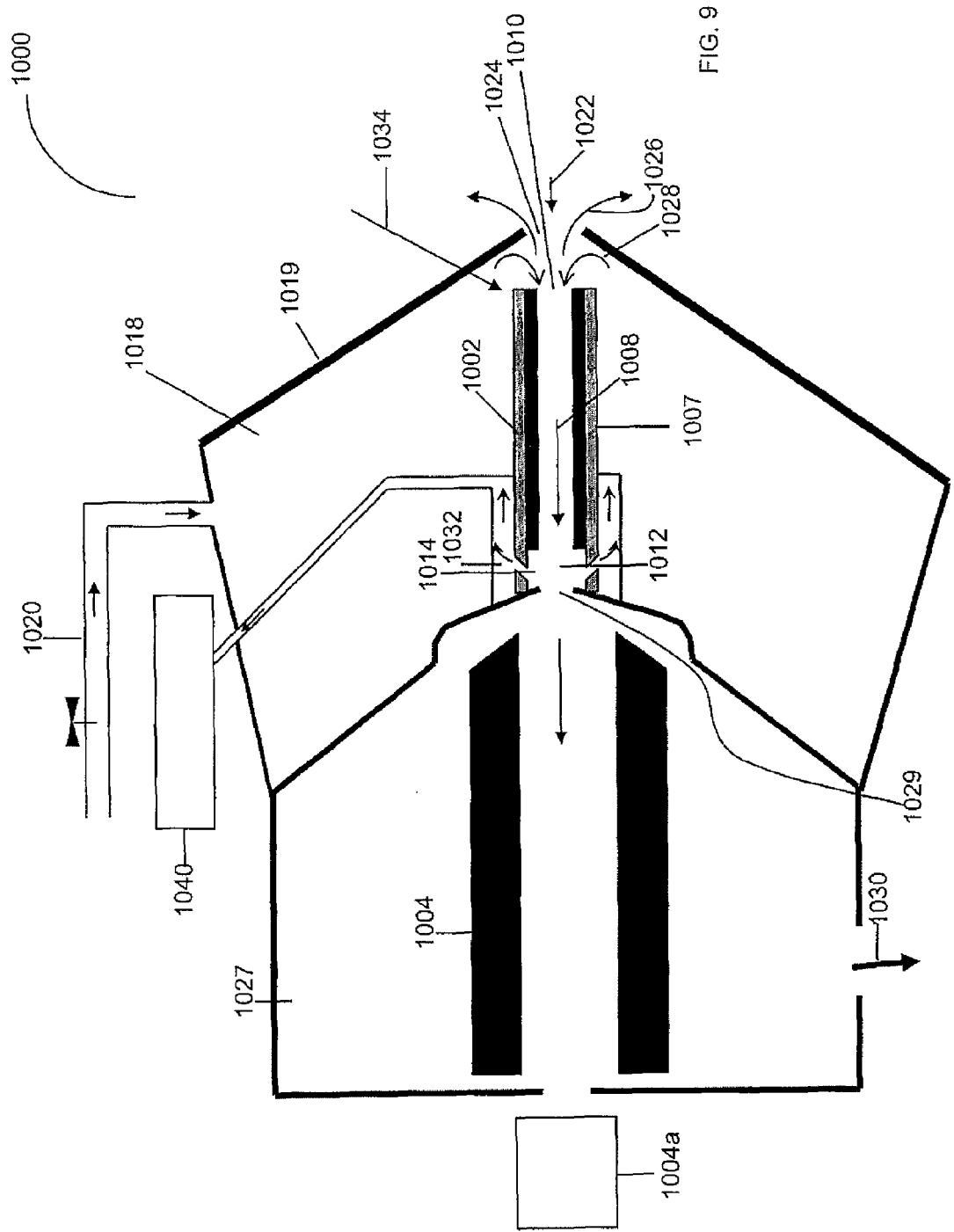
FIG. 9, in a schematic view, illustrates a differential mobility spectrometer/mass spectrometer system including a juncture chamber from which a bleed gas is drawn between the differential mobility spectrometer and the mass spectrometer in accordance with an aspect of a ninth embodiment of the present invention.

Referring to FIG. 9, there is illustrated in a schematic view a differential mobility spectrometer/mass spectrometer system 1000 in accordance with an aspect of ninth embodiment of the present invention. For clarity, the same reference numerals used in FIG. 1, with 800 added, are used in FIG. 9 to designate elements analogous to the elements of FIG. 1. For brevity, the description of preceding figures, including FIG. 1, are not repeated with respect to FIG. 9.

As shown in FIG. 9, the system 1000 is quite similar to the systems 200 and 300 of FIGS. 1 and 2 respectively. However, instead of adding a throttle gas to the juncture chamber 1014, the system 1000 of FIG. 9 comprises a gas outlet 1032 including a vacuum pump 1040 for drawing a bleed gas out of the juncture chamber 1014. As the quantity of bleed gas drawn out of the juncture chamber 1014 increases, the gas flow rate of the drift gas 1008 within the differential mobility spectrometer 1002 will increase, which can diminish selectivity and resolution, while, at the same time, increasing sensitivity. For this reason, in the system 1000 of FIG. 9, the differential mobility spectrometer 1002 can be dimensioned to provide, initially, a relatively long residence time for the ions 1022 within the differential mobility spectrometer 1002, and a relatively low gas flow rate of the drift gas 1008 within the differential mobility spectrometer 1002. This initial bias of the differential mobility spectrometer 1002 in favor of selec- tivity at the expense of sensitivity can be subsequently offset by increasing a vacuum draw provided by vacuum pump 1040 to increase the rate at which bleed gas is drawn from the juncture chamber 1014 to increase the flow rate of the drift gas.

The bleed gas may also be useful for DMS/MS systems where the mass spectrometer inlet is sized to provide either a discontinuous gas flow into vacuum, or a very low gas flow rate. As known in the art, a very small diameter orifice can provide a very low gas flow rate into the vacuum system, and an inlet diaphragm or adjustable orifice dimension may provide a discontinuous or variable gas flow into the mass spectrometer vacuum system. Under these conditions, as described below in more detail, the bleed gas draw can provide a continuous flow of carrier gas through the DMS cell regardless of the flow rate into the vacuum system of the mass spectrometer system.

For example, drawing a bleed gas from the juncture of a differential mobility spectrometer and a mass spectrometer can be used to match the higher flow capacity of the differential mobility spectrometer with the lower flow capacity of a low-flow, low-cost, portable mass spectrometer. Because pumping capacity can be the primary limitation in reducing the size and weight of a mass spectrometer, this pumping capacity can be sacrificed to provide a smaller mass spectrometer. To compensate for this lower pumping capacity, a shutter can be provided at the orifice or inlet to the vacuum chamber. This shutter might have a duty cycle of, say, 1%, so that it is open for 10 milliseconds, and then closed for one second (1000 milliseconds), to reduce the load on the vacuum pump.

However, the flows through the differential mobility spectrometer can be, and preferably are, continuous. Thus, to avoid turbulence or other problems, as shown in FIG. 9 a bleed gas can be drawn from the juncture of the differential mobility spectrometer with the mass spectrometer. By extracting gas from this juncture region, a high fraction of the differential mobility spectrometer-filtered ions can enter the vacuum chamber inlet, while excess flow through the differential mobility spectrometer can be exhausted as bleed gas. This bleed gas flow can prevent or reduce turbulence in the differential mobility spectrometer and maintain a constant differential mobility spectrometer resolution.

Figure 10:
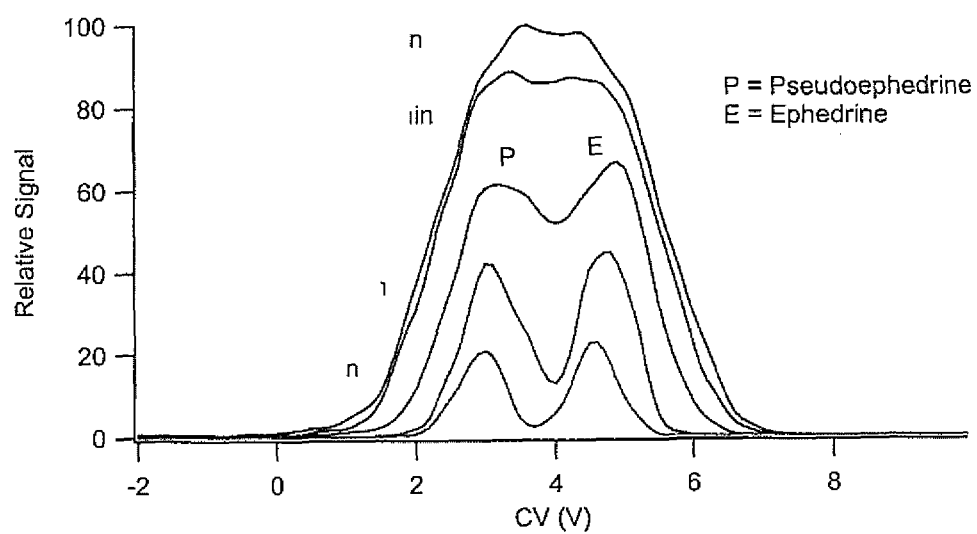
FIG. 10, in a series of graphs, illustrates different resolutions of a CV scan for separation of a sample containing ephedrine and pseudoephedrine using a fixed differential mobility spectrometer geometry with a variable amount of throttle gas added at the juncture of the differential mobility spectrometer and the mass spectrometer.

Referring to FIG. 10, there is illustrated in a series of graphs, the effect of throttle gas on the resolution and peak width for a sample containing ephedrine and pseudoephedrine. The differential mobility spectrometer electrode dimension was 1×10×300 mm. RF was set to approximately 4000 V peak to peak amplitude. In each graph, CV voltage is plotted on the x axis, while original signal intensity is plotted on the y axis normalized to the signal intensity achieved with no throttle gas provided.

As shown the compensation voltage peak width decreases (improved selectivity) as more throttle gas is added to the juncture chamber, while sensitivity correspondingly diminishes. That is, the top trace in FIG. 10, trace 100, shows that data generated when the DMS electrode set is optimized for sensitivity, and no throttle gas is provided. In this case, the mobility peaks for pseudoephedrine and ephedrine are merged to give a single peak with very broad half width. As the volumetric flow of throttle gas increases, from the trace 102 representing a throttle gas flow rate of 0.4 L/min, to trace 104, representing a throttle gas flow rate of 0.8 L/min two distinct peaks begin to become apparent as a result of the selectivity improvement achieved by narrowing each of the mobility peaks. When the throttle gas is set to approximately 1.4 L/min, the peak centers are sufficiently resolved to achieve separation of these two components, although the sensitivity has decreased by approximately a factor of 2. Further increases in the throttle gas flow provide higher resolution, although the sensitivity loss also becomes greater, as shown in trace 108, representing a throttle gas flow rate of 1.8 L/min.

Accordingly, according to some aspects of these embodiments of the present invention, a throttle gas can be added to the juncture chamber until an acceptable compromise between sensitivity and selectivity is reached, such that sensitivity remains at a level to enable the peaks to be discerned, while selectivity has been improved to enable the peaks to be readily distinguished.

According to some aspects of some other embodiments of the present invention, in which no throttle gas is provided, but instead a bleed gas is drawn from the juncture chamber, the initial mass spectrum obtained may show peaks that are distinguishable, but which represent very faint signals, given the loss of sensitivity due to the very high residence times within the differential mobility spectrometer. According to these aspects of the present invention, increasing amounts of bleed gas can be drawn from the juncture chamber to increase the gas flow rate through the differential mobility spectrometer, thereby reducing the residence time of ions within the differential mobility spectrometer (the electrode geometry having been selected to provide this long residence time). As this occurs, the peak height will increase, representing the greater sensitivity, but may also become broader and overlap. By observing this process, an operator can stop increasing the bleed gas flow rate at a point where the peaks are still readily distinguishable and sensitivity is still acceptable.

According to some aspects of various embodiments of the present invention, a method of operating mass spectrometer systems as defined above is provided in which the differential mobility spectrometer is maintained at an internal operating pressure (the curtain chamber operating pressure), while the mass spectrometer is maintained at a vacuum pressure that is substantially lower than the internal operating pressure. The differential mobility spectrometer is also in fluid communication with the mass spectrometer to draw a gas flow, including ions provided to the differential mobility spectrometer, through the differential mobility spectrometer and into a vacuum chamber containing the mass spectrometer. A gas flow between the differential mobility spectrometer and the mass spectrometer can be modified to change the gas flow rate within the differential mobility spectrometer without changing the total volumetric flow rate into the mass spectrometer. As described above, this gas flow rate can be modified, for example, by adding a throttle gas at a throttle gas flow rate to the gas flow between the differential mobility spectrometer and the mass spectrometer to decrease the gas flow rate through the differential mobility spectrometer. Optionally, the throttle gas flow rate can be varied to vary the decreases in the gas flow rate.

Optionally the method further comprises detecting the ions drawn into the mass spectrometer to provide a mass spectrum. Initially, the electrode geometry of the differential mobility spectrometer may be selected to provide good sensitivity but poor selectivity. Then, an operator can select a selected resolution for the mass spectrum and determine and then adjust the gas flow rate to provide the selected resolution. The operator can then vary the throttle gas flow rate to decrease the gas flow rate to provide the adjusted gas flow rate to provide the selected resolution for the mass spectrum, by increasing a residence time of the ions within the differential mobility spectrometer. This can also have the result of decreasing sensitivity somewhat, however.

Optionally, an outlet of the differential mobility spectrometer can be connected to an inlet of the mass spectrometer to define an ion path of travel for ions therebetween using a juncture chamber. In such embodiments, the throttle gas can be directed into the juncture chamber and away from the ion path of travel to reduce disruption of the ion path of travel by the throttle gas. Alternatively, the throttle gas can simply be dispersed throughout the juncture chamber.

Optionally, the selected resolution for the mass spectrum and the adjusted gas flow rate for providing this selected resolution can be determined substantially contemporaneously. For example, these steps can be performed substantially contemporaneously with the step of varying the throttle gas flow rate, whereby an operator can simply observe how the resolution of the mass spectrum changes (along with the sensitivity) as the throttle gas flow rate is increased. Then, after an operator reaches an acceptable resolution (while retaining acceptable sensitivity), the throttle gas flow rate can be maintained at a constant level, thereby determining the adjusted gas flow rate to provide the selected resolution of the mass spectrum.

According to aspects of other embodiments of the present invention, instead of supplying a throttle gas to a juncture chamber between the differential mobility spectrometer and the mass spectrometer, a bleed gas can be drawn from the gas flow between the differential mobility spectrometer and the mass spectrometer at a bleed gas flow rate to increase a gas flow rate through the differential mobility spectrometer. The bleed gas flow rate can be varied to vary the increase in the gas flow rate. That is, in embodiments in which a bleed gas is drawn from the gas flow between the differential mobility spectrometer and the mass spectrometer, an electrode geometry of the differential mobility spectrometer can initially be selected to provide good selectivity at the price of poor or very poor sensitivity. Then, sensitivity can be improved, while selectivity is diminished, by increasing the bleed gas flow rate of the bleed gas drawn from the gas flow between the differential mobility spectrometer and the mass spectrometer.

According to some aspects of some embodiments of the present invention, an operator can determine a selected transmission sensitivity, determine an adjusted gas flow rate to provide the selected transmission sensitivity, and vary the bleed gas flow rate to provide the increase in the gas flow rate to provide the adjusted gas flow rate to provide the selected transmission sensitivity. Optionally, the steps can be performed altogether. That is, an operator can gradually increase a vacuum pump speed connected to the juncture chamber to increase the bleed gas flow rate, observing at the same time from the mass spectrum how the selected transmission sensitivity improves. Then, once an acceptable transmission sensitivity has been reached (and while selectivity is still acceptable) the bleed gas flow rate can be maintained to provide the adjusted gas flow rate to provide the selected transmission sensitivity. For example, for a given separation, an operator may try to optimize the sensitivity by seeing how much selectivity is required to eliminate an interference, and then maximizing the sensitivity while still removing the interference.

Figure 11:
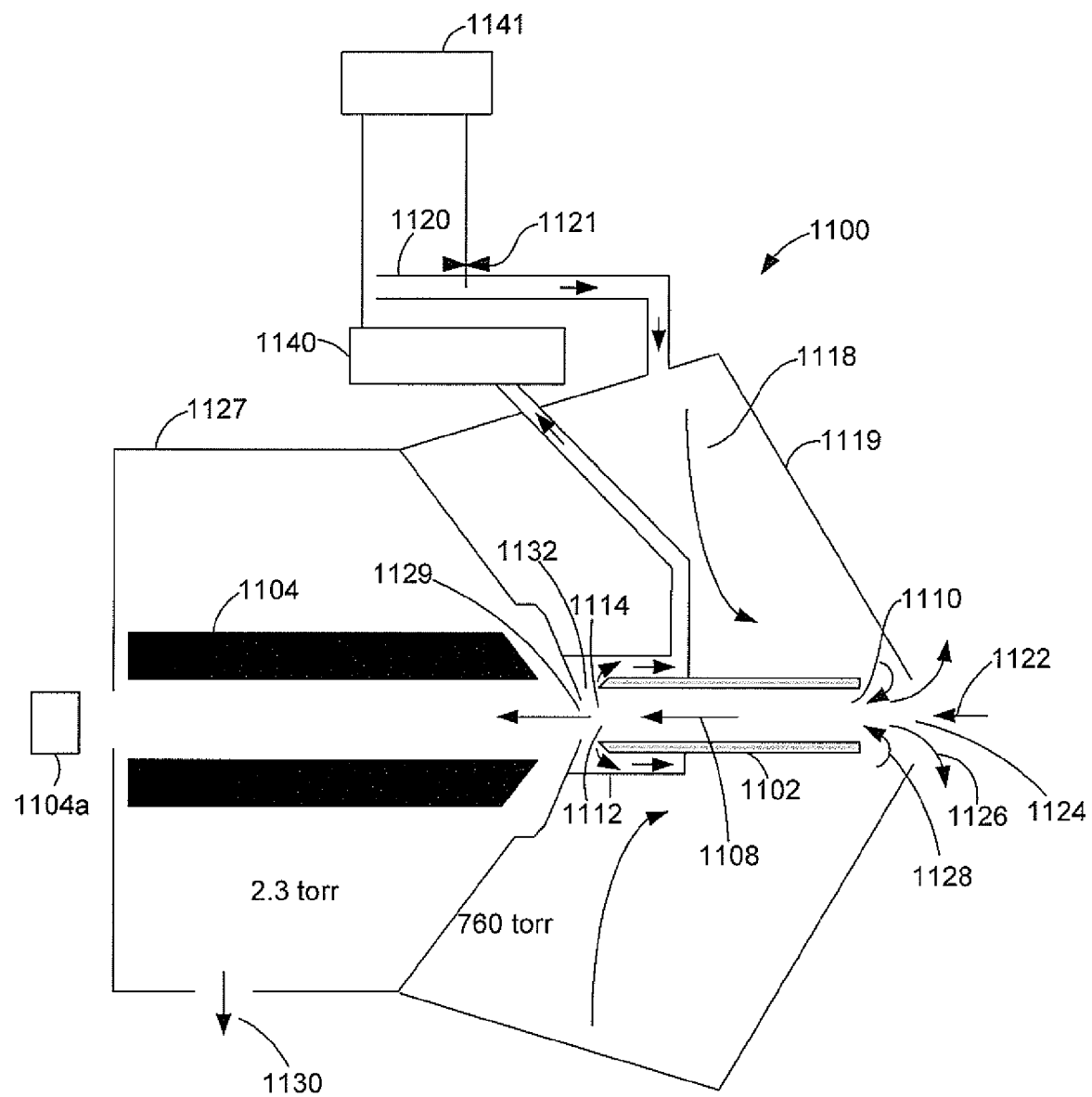
FIG. 11, in a schematic view, illustrates a mass spectrometer system including a juncture chamber from which a bleed gas is drawn between an upstream heated tube and a downstream mass spectrometer in accordance with an aspect of a tenth embodiment of the present invention.

Referring to FIG. 11, there is illustrated in a schematic view, a mass spectrometer system 1100 in accordance with an aspect of a tenth embodiment of the present invention. The mass spectrometer system 1100 comprises a first vacuum lens element 1104 of a mass spectrometer (hereinafter generally designated mass spectrometer 1104), but does not include a differential mobility spectrometer. Lens element 1104 is contained within a vacuum chamber 1127. The mass spectrometer 1104 also comprises mass analyzer elements 1104*a* downstream from the vacuum chamber 1127. Ions can be transported through the vacuum chamber 1127 and may be transported through one or more additional differentially pumped vacuum stages prior to the mass analyzer indicated schematically as mass analyzer 1104a, as described, for example, with respect to the embodiment of FIG. 1.

A heated tube 1102 can be provided upstream of vacuum chamber 1127. Similar to the plates of the differential mobility spectrometers of the embodiments described above, the heated tube 1102 can surround a drift gas 1108 that can drift from an inlet 1110 of the heated tube 1102 to an outlet 1112 of the heated tube 1102. The outlet 1112 of the heated tube 1102 can release a drift gas 1108 into a juncture chamber 1114. The juncture chamber 1114 defines a path of travel for ions between the heated tube 1102 and the mass spectrometer 1104. In some embodiments the outlet of 1112 of the heated tube 1102 can be aligned with the inlet of the mass spectrometer 1104 to define an ion path of travel there between, while walls of the juncture chamber 1114 can be spaced from this path of travel to limit interference with the ions 1122 traveling along the path of travel.

The heated tube 1102 and juncture chamber 1114 are both contained within a curtain chamber 1118 defined by a curtain plate (boundary member) 1119 and supplied with a curtain gas from a curtain gas source 1120. The curtain gas source 1120 can provide the curtain gas to the interior of the curtain chamber 1118. Ions 1122 can be provided from an ion source (not shown) and can be emitted into the curtain chamber 1118 via curtain chamber inlet 1124. The curtain gas can be supplied to the curtain chamber at a rate sufficient to provide both a curtain gas outflow out of the curtain chamber inlet, as well as a curtain gas inflow into the heated tube. The diameter of the inlet 1110 of the heated tube 1102 can be substantially larger than a vacuum chamber inlet (or mass spectrometer inlet) 1129, such that the heated tube 1102 does not restrict gas flow. The pressure of the curtain gas within the curtain chamber 1118 can provide both a curtain gas outflow 1126 out of the curtain gas chamber inlet 1124, as well as a curtain gas inflow 1128 into the heated tube 1102, which inflow 1128 can become the drift gas 1108 for carrying the ions 1122 through the heated tube 1102 and into the juncture chamber 1114. The curtain plate 1119 may be connected to a power supply to receive an adjustable DC potential.

Similar to the embodiment of FIG. 1, the vacuum chamber 1127 can be maintained at a much lower pressure than the curtain chamber 1118. In accordance with an aspect of an embodiment of the present invention, the vacuum chamber 1127 can be maintained at a pressure of 2.3 Torr via vacuum pump 1130. In an example, an internal pressure of the heated tube 1102 can be maintained at a pressure of 760 Torr. As a result of the significant pressure difference between the curtain chamber 1118 and the vacuum chamber 1127, the drift gas 1108 can be drawn through the heated tube 1102, the juncture chamber 1114 and vacuum chamber inlet 1129 into the vacuum chamber 1127 and the first vacuum lens element 1104.

From the foregoing, it can be seen that the mass spectrometer system 1100 of the FIG. 11 is, in some respects, quite similar to the systems 200 and 300 of FIGS. 1 and 2 respectively. However, instead of adding a throttle gas to the juncture chamber 1114, the system 1100 of FIG. 11 comprises a gas outlet 1132 including an additional vacuum pump 1140 for drawing a bleed gas out of the juncture chamber 1114. The gas flow drawn from gas outlet 1132 by additional vacuum pump 1140 can draw a larger fraction of ions into the heated tube 1102.

The increased gas flow through the heated tube 1102 can also lower the residence time for ions within the heated tube 1102, thereby lowering diffusion losses and increasing sensitivity as mentioned above. The curtain gas flow rate can be increased proportionately to the vacuum pump flow rate to ensure that sufficient gas to provide an outflow from gas chamber inlet 1124.

In these respects, the system 1100 is quite similar to the system 1000 of FIG. 9. However, the system 1100 differs from the system 1000 in FIG. 9 in that the system 1100 does not include a differential mobility spectrometer. Instead, the differential mobility spectrometer has simply been replaced with a heated tube 1102.

In accordance with an aspect of an embodiment of the invention, the system 1100 of FIG. 11 can also comprise a controller 1141. Controller 1141 can comprise a computer processor, together with suitable user input/output modules. In one embodiment, a user can adjust vacuum pump 1140 (which can be any suitable device for drawing a gas flow) to adjust a rate at which bleed gas is drawn out of the juncture chamber 1114. In this embodiment, controller 1141 can monitor the rate at which vacuum pump 1140 draws bleed gas out of the juncture chamber 1114, and then can calculate a suitable increase in curtain gas flow to be provided by curtain gas source 1120, and can adjust a curtain gas flow meter 1121 to provide this increase in curtain gas flow. Alternatively vacuum pump 1140 can be maintained at a constant rate, and a adjustable restriction such as an aperture may be located between pump 1140 and the juncture chamber. According to some embodiments, an increase in bleed gas flow rate will be matched by an equal increase in curtain gas inflow rate. According to other embodiments, recognizing that some of this increase in curtain gas inflow may increase flow 1126 out of curtain chamber inlet 1124, the curtain gas inflow may be increased by more than the increase in the bleed gas flow rate.

According to another embodiment of the invention, vacuum pump 1140 may not be directly controlled by an operator. Instead, an operator can control vacuum pump 1140 via controller 1141, and controller 1141 could then determine, using for example, a computer processor, a suitable corresponding adjustment to be made to the curtain gas flow rate.

Figure 12:
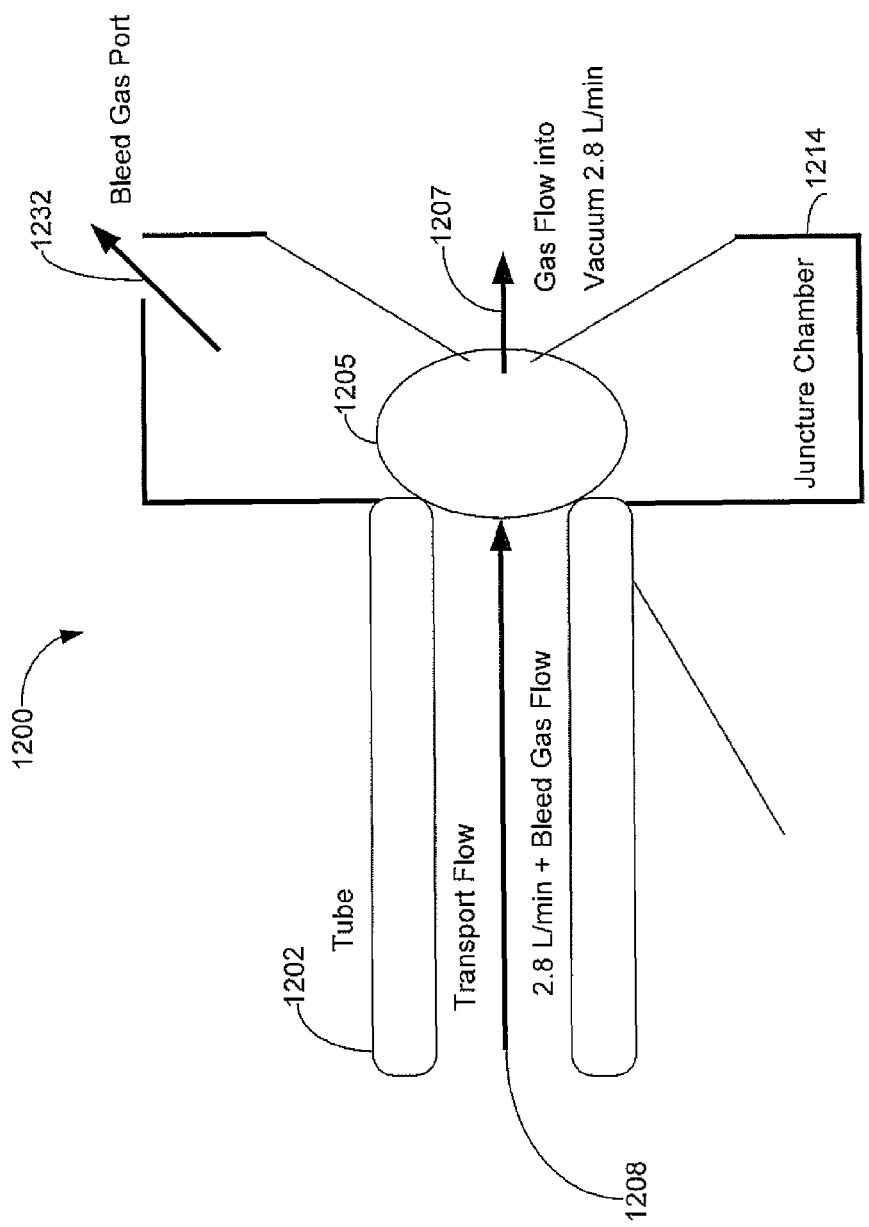
FIG. 12, in a schematic view, illustrates a mass spectrometer system including a juncture chamber from which a bleed gas is drawn between an upstream heated tube and a downstream mass spectrometer, wherein an electric field is provided within the juncture chamber to guide ions into the mass spectrometer and to impede ions from being drawn out of the juncture chamber with the bleed gas in accordance with an aspect of a further embodiment of the invention.

According to some embodiments in which bleed gas is drawn from the juncture chamber, ions may tend to follow streamlines directed out of the bleed gas outlet in the juncture chamber. Referring to FIG. 12, there is illustrated in a schematic diagram a portion of a mass spectrometer system 1200 in accordance with an aspect of another embodiment of the invention. The mass spectrometer system 1200 comprises an upstream heated tube 1202 and a juncture chamber 1214. The juncture chamber 1214 is located downstream of the heated tube 1202 to receive drift gas entrained ions 1208 from the heated tube 1202. As illustrated, a bleed gas can be drawn through bleed gas port 1232 to increase the drift gas flow rate of drift gas 1208 through heated tube 1202. On its own, the gas outlet 1232 might tend to create streamlines of bleed gas that could entrain ions and draw them out through gas port 1232. To impede this, a suitable electric field 1205 can be provided around the drift gas 1208 where the drift gas 1208 enters the juncture chamber. The electric field can be configured to guide the entrained ions within streamlines drawn into a vacuum chamber (not shown) and to impede the ions from being drawn by other streamlines through the bleed gas port 1232. Suitable ion optical elements, known to those of skill in the art, such as, for example, a single or multiple ion lens elements with DC or RF potentials applied, can be used to provide the electric field 1205. More generally, and referring to FIG. 11, a potential difference between the heated tube outlet 1112 and vacuum chamber inlet 1129 can help direct ions across the gap between the outlet 1112 and the mass spectrometer inlet. The ions can exit the heated tube 1102, traveling on-axis with respect to the downstream inlet orifice, while the bleed gas can be drawn radially away from the inlet. In this configuration, a potential difference between the tube outlet 1112 and vacuum chamber inlet 1129 can help to keep ions moving in the axial direction with the gas flow into vacuum chamber 1127.

EXPERIMENTAL RESULTS

The operation of the mass spectrometer system 1100 of FIG. 11, which lacks a DMS, can be simulated to some extent by operating a mass spectrometer system similar to the system 1100, except that this mass spectrometer system comprises a DMS. This DMS can be run in transparent mode to allow all of the ions to be transmitted without discrimination, when the separation voltage is turned off, or set sufficiently low to prevent differential mobility separations, and the compensation voltage is set to 0. Additionally, in this mode of operation the DMS can simultaneously transmit ions of both polarities and subject each to separation based on their differential mobility constants.

According to an aspect of an embodiment of a present invention, a mass spectrometer system similar to the mass spectrometer system 1000 of FIG. 9 was operated in transparent mode, with separation voltage and compensation voltage set to 0 volts. The dimensions of the tube or DMS cell were 1×10×30 mm (while the cross section was rectangular for the collection of these data, any suitable cross-section could have been be used, such as a typical circular cross section for a tube). The gas flow into the vacuum, drawn through the tube, was 2.8 L/minute. The curtain gas inflow was set to 3.3 L/minute to provide a 0.5 L/minute outflow from the curtain plate. Operating this mass spectrometer system in this manner results in the DMS cell essentially acting as a tube with two conductive walls and two insulating walls.

Initially, the vacuum pump for drawing bleed gas from the juncture chamber was off. In this mode of operation, the DMS-MS signal provided by the mass analyzer elements downstream of the mass spectrometer was approximately 100000 cps (counts per second). Subsequently, after about a minute, the vacuum pump for drawing the bleed gas out of the juncture chamber was turned on to draw an additional flow of 3.7 L/minute out from the juncture chamber. Adding this 3.7 L/minute bleed gas outflow, to the 2.8 L/minute gas flow through the tube resulting from the pressure differential between vacuum chamber 1127 and the internal pressure of the DMS, resulted in a total gas flow through the "tube" of 6.5 L/minute. The curtain gas inflow was not increased at this point, thereby eliminating the beneficial outflow from the curtain plate. Nonetheless, the signal provided at the downstream mass analyzer elements increased to 540000 cps.

Subsequently the curtain gas inflow was re-optimized to 7.1 L/minute (to take into account the bleed gas drawn out) and to once again provide an outflow of approximately 0.6 L/minute (7.1 L/minute inflow−6.5 L/minute outflow through the 'tube"). As a result, the signal increased to 760,000 cps. These results show significant gains when pumping at the exit of the 'tube" (i.e. drawing the bleed gas out from the juncture chamber). These gains may be partially due to reduced residence time and diffusion within the "tube" or DMS, and possibly, more significantly due to amplifying the inlet gas flow to draw more ions into the "tube" and reduce losses at the inlet.

Similar experimental results were obtaining using this mass spectrometer system, while varying the pump speed of the vacuum pump for drawing the bleed gas from the juncture chamber. When the vacuum pump was off, such that a 2.8 L/minute transport gas flow including minoxidil was drawn through the "tube", the signal for a sample of minoxidil was 124,000 cps as measured at the downstream mass analyzer element This signal intensity was improved when the bleed gas was drawn at 3.7 L/minute, to provide a total transport gas flow through the "tube", of 6.5 L/minute. At that transport flow rate, the signal intensity increased to 620000 cps. Further improvements in the signal intensity were observed when the bleed gas flow rate was increased 4.9 L/minute to give a total transport flow rate through the "tube" of 7.7 L/minute. At that transport gas flow through the signal intensity increased further to 730000 cps. In all of these cases, the curtain gas inflow was increased directly and proportionately with the increases in bleed gas flow to provide a relatively constant curtain gas outflow out of the curtain gas chamber inlet.

While the Applicant's teachings are described in conjunction with various embodiments, it is not intended that the Applicant's teachings be limited to such embodiments.

The invention claimed is:

1. A mass spectrometer system comprising:
an ion conduit for receiving a gas flow and ions from an ion source, the ion conduit having an internal operating pressure, the ion conduit being sized such that the ion conduit does not restrict gas flow;
a boundary member defining a curtain gas chamber containing the ion conduit;
a curtain gas supply for providing a curtain gas directed by the boundary member to an inlet of the ion conduit to dry and decluster the ions and to provide a gas flow into the ion conduit, and a curtain gas outflow out of a curtain gas chamber inlet;
a mass spectrometer at least partially sealed to, and in fluid communication with, the ion conduit for receiving the ions from the ion conduit;
a vacuum chamber surrounding the mass spectrometer for maintaining the mass spectrometer at a vacuum pressure lower than the internal operating pressure, such that the vacuum chamber is operable to draw the gas flow including the ions through the ion conduit and into the vacuum chamber; and,
a gas outlet for drawing a gas outflow from the gas flow located between the ion conduit and the mass spectrometer to increase the gas flow rate through the ion conduit, the gas outlet being located between the ion conduit and the mass spectrometer.

2. The mass spectrometer system as defined in claim 1 further comprising at least one heater for heating at least one of the curtain gas, a throttle gas, a heated zone upstream of the inlet of the ion conduit, an inlet of the mass spectrometer and the ion conduit to decluster the ions.

3. The mass spectrometer system as defined in claim 1 wherein the gas outlet is adjustable to vary the gas outflow from the gas flow and vary the increase in the gas flow rate.

4. The mass spectrometer system as defined in claim further comprising a juncture chamber connecting an outlet of the ion conduit to an inlet of the mass spectrometer to define an ion path of travel there between, the gas outlet being located in the juncture chamber.

5. The mass spectrometer system as defined in claim 4 wherein
the outlet of the ion conduit is aligned with the inlet of the mass spectrometer to transmit the ions substantially along the path of travel to the inlet of the mass spectrometer; and, the juncture chamber comprises a side wall spaced from the path of travel.

6. The mass spectrometer system as defined in claim 1 wherein the ion conduit comprises a differential mobility spectrometer for receiving ions from the ion source.

7. The mass spectrometer system as defined in claim 1 further comprising an electrical field generator for providing an electrical field between the ion conduit and the vacuum chamber, the electrical field generator being configured to generate an electrical field to guide the ions into the vacuum chamber and to impede ions from being drawn out of the gas outlet.

8. The mass spectrometer system as defined in claim 1 wherein the ion conduit is a differential mobility spectrometer.

9. The mass spectrometer system as defined in claim 2 wherein the at least one heater is operable to heat the inlet of the ion conduit to decluster the ions.

10. A method of operating a mass spectrometer system including an ion conduit contained in a curtain gas chamber, and a mass spectrometer contained in a vacuum chamber at least partially sealed to, and in fluid communication, with, the ion conduit, the method comprising:
   a) maintaining the ion conduit at an internal operating pressure by directing a curtain gas to an inlet of the ion conduit to dry and decluster the ions and to provide a variable gas flow into the ion conduit;
   b) providing a curtain gas outflow out of a curtain gas chamber inlet of the curtain gas chamber;
   c) providing ions to the ion conduit;
   d) maintaining the mass spectrometer at a vacuum pressure lower than the internal operating pressure to draw the gas flow including the ions through the ion conduit and into the vacuum chamber; and,
   e) drawing a bleed gas at a bleed gas flow rate from the gas flow between the ion conduit and the mass spectrometer to increase a gas flow rate through the ion conduit.

11. The method as defined in claim 10 wherein e) further comprises varying the bleed gas flow rate to vary the increase in the gas flow rate.

12. The method as defined in claim 11 further comprising determining a selected transmission sensitivity;
   determining an adjusted gas flow rate to provide the selected transmission sensitivity; and,
   varying the bleed gas flow rate to provide the increase in the gas flow rate to provide the adjusted gas flow rate to provide the selected transmission sensitivity.

13. The method as defined in claim 12 wherein selecting the transmission sensitivity and determining the adjusted gas flow rate to provide the selected transmission sensitivity are substantially contemporaneous.

14. The method as defined in claim 10 wherein the ion conduit comprises a differential mobility spectrometer for receiving ions from the ion source, the differential mobility spectrometer having electrodes and at least one voltage source for providing DC and RF voltages to the electrodes, and the method further comprises operating the differential mobility spectrometer in transparent mode such that the RF voltage provided to the electrodes is zero Volts.

15. The method as defined in claim 14 wherein the DC voltage provided to the electrodes is zero Volts.

16. The method as defined in claim 10 further comprising heating the ion conduit to decluster the ions.

17. The method as defined in claim 10 further comprising providing an electrical field between the ion conduit and the vacuum chamber, the electrical field being configured to guide the ions into the vacuum chamber and to impede ions from being drawn out of the gas flow and into the bleed gas flow.

18. The method as defined in claim 17 wherein the ion conduit is a differential mobility spectrometer, and the method further comprises operating the differential mobility spectrometer in transparent mode with a compensation voltage of zero volts.

19. The method as defined in claim 18 wherein the method further comprises operating the differential mobility spectrometer in transparent mode with a separation voltage of zero volts.

* * * * *